United States Patent
el Kaliouby et al.

(10) Patent No.: US 10,922,566 B2
(45) Date of Patent: *Feb. 16, 2021

(54) COGNITIVE STATE EVALUATION FOR VEHICLE NAVIGATION

(71) Applicant: Affectiva, Inc., Boston, MA (US)

(72) Inventors: Rana el Kaliouby, Milton, MA (US); Abdelrahman N. Mahmoud, Somerville, MA (US); Seyedmohammad Mavadati, Watertown, MA (US); Panu James Turcot, Pacifica, CA (US)

(73) Assignee: Affectiva, Inc., Boston, MA (US)

( * ) Notice: Subject to any disclaimer, the term of this patent is extended or adjusted under 35 U.S.C. 154(b) by 298 days.

This patent is subject to a terminal disclaimer.

(21) Appl. No.: 15/975,007

(22) Filed: May 9, 2018

(65) Prior Publication Data

US 2018/0330178 A1 Nov. 15, 2018

Related U.S. Application Data

(60) Provisional application No. 62/503,485, filed on May 9, 2017.

(51) Int. Cl.
*G06K 9/00* (2006.01)
*A61B 5/00* (2006.01)
(Continued)

(52) U.S. Cl.
CPC ........ *G06K 9/00845* (2013.01); *A61B 5/1079* (2013.01); *A61B 5/1128* (2013.01);
(Continued)

(58) Field of Classification Search
USPC .......................................................... 701/1
See application file for complete search history.

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.

(Continued)

*Primary Examiner* — Tyler D Paige
(74) *Attorney, Agent, or Firm* — Adams Intellex, PLC

(57) ABSTRACT

Disclosed embodiments provide cognitive state evaluation for vehicle navigation. The cognitive state evaluation is accomplished using a computer, where the computer can perform learning using a neural network such as a deep neural network (DNN) or a convolutional neural network (CNN). Images including facial data are obtained of a first occupant of a first vehicle. The images are analyzed to determine cognitive state data. Layers and weights are learned for the deep neural network. Images of a second occupant of a second vehicle are collected and analyzed to determine additional cognitive state data. The additional cognitive state data is analyzed, and the second vehicle is manipulated. A second imaging device is used to collect images of a person outside the second vehicle to determine cognitive state data. The second vehicle can be manipulated based on the cognitive state data of the person outside the vehicle.

25 Claims, 20 Drawing Sheets

(51) Int. Cl.

| | | |
|---|---|---|
| *G06K 9/46* | (2006.01) | |
| *G16H 50/20* | (2018.01) | |
| *G06N 3/08* | (2006.01) | |
| *B60W 50/14* | (2020.01) | |
| *G06N 5/04* | (2006.01) | |
| *B60W 50/08* | (2020.01) | |
| *A61B 5/18* | (2006.01) | |
| *A61B 5/16* | (2006.01) | |
| *G06K 9/62* | (2006.01) | |
| *A61B 5/11* | (2006.01) | |
| *A61B 5/107* | (2006.01) | |
| *G16H 30/40* | (2018.01) | |
| *G06N 3/04* | (2006.01) | |
| *G16H 50/30* | (2018.01) | |
| *G06N 3/02* | (2006.01) | |
| *A61B 5/024* | (2006.01) | |
| *A61B 5/0531* | (2021.01) | |
| *A61B 5/01* | (2006.01) | |
| *A61B 5/08* | (2006.01) | |

(52) U.S. Cl.
CPC ............ *A61B 5/165* (2013.01); *A61B 5/18* (2013.01); *A61B 5/6893* (2013.01); *A61B 5/7267* (2013.01); *A61B 5/746* (2013.01); *B60W 50/082* (2013.01); *B60W 50/14* (2013.01); *G06K 9/00228* (2013.01); *G06K 9/00302* (2013.01); *G06K 9/00369* (2013.01); *G06K 9/4628* (2013.01); *G06K 9/627* (2013.01); *G06N 3/0454* (2013.01); *G06N 3/084* (2013.01); *G06N 5/046* (2013.01); *G16H 30/40* (2018.01); *G16H 50/20* (2018.01); *G16H 50/30* (2018.01); *A61B 5/0022* (2013.01); *A61B 5/01* (2013.01); *A61B 5/02405* (2013.01); *A61B 5/02416* (2013.01); *A61B 5/0531* (2013.01); *A61B 5/0816* (2013.01); *A61B 5/4266* (2013.01); *A61B 2503/22* (2013.01); *A61B 2576/00* (2013.01); *B60W 2050/143* (2013.01); *G06N 3/02* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | MacLean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |

(56) References Cited

U.S. PATENT DOCUMENTS

| | | |
|---|---|---|
| 8,022,831 B1 | 9/2011 | Wood-Eyre |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,738,523 B1 | 5/2014 | Sanchez et al. |
| 8,947,217 B2 | 2/2015 | Moussa et al. |
| 10,627,817 B2 * | 4/2020 | Zijderveld ............ A61B 5/0077 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1 * | 1/2006 | Brockway ............... B60T 17/18 180/272 |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1 | 6/2010 | Ahn et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0083075 A1 * | 4/2011 | MacNeille ............ G10L 15/22 715/728 |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0257985 A1 * | 10/2011 | Goldstein ........... G06F 16/5838 705/1.1 |
| 2011/0263946 A1 | 10/2011 | el Kaliouby et al. |
| 2012/0109452 A1 | 5/2012 | Autran et al. |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2013/0204455 A1 * | 8/2013 | Chia .................... G07C 5/0808 701/1 |
| 2014/0171752 A1 | 6/2014 | Park et al. |
| 2014/0172910 A1 | 6/2014 | Jung et al. |
| 2014/0218187 A1 * | 8/2014 | Chun ...................... A61B 5/18 340/439 |
| 2015/0258995 A1 | 9/2015 | Essers et al. |
| 2016/0104486 A1 | 4/2016 | Penilla et al. |
| 2017/0003784 A1 | 1/2017 | Garg et al. |
| 2017/0337438 A1 * | 11/2017 | El Kaliouby, Jr. .. A61B 5/1103 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG—EBGM." Pattern Recognition Letters 29.10 (2008): 1537-1543.

Fasel, B. (Aug. 2002). Robust face analysis using convolutional neural networks. In Object recognition supported bu user interaction for service robots (vol. 2, pp. 40-43). IEEE.

Matsugu, M., Mori, K., Mitari, Y., & Kaneda, Y. (2003). Subject independent facial expression recognition with robust face detection

(56) References Cited

OTHER PUBLICATIONS using a convolutional neural network. Neural Networks, 16(5-6), 555-559.

* cited by examiner

COGNITIVE STATE EVALUATION FOR VEHICLE NAVIGATION

RELATED APPLICATIONS

This application claims the benefit of U.S. provisional patent application "Vehicle Artificial Intelligence Evaluation of Mental States" Ser. No. 62/503,485, filed May 9, 2017. The foregoing application is hereby incorporated by reference in its entirety.

FIELD OF ART

This application relates generally to vehicle manipulation and more particularly to cognitive state evaluation for vehicle navigation.

BACKGROUND

Human cognitive states which can include emotions are often manifested in facial expressions. The human face contains over forty muscles acting in coordination to produce myriad facial expressions. The facial expressions can represent cognitive states such as anger, fear, sadness, disgust, contempt, surprise, and happiness. Facial muscles form the facial expressions by brow raising, smiling, nose wrinkling, and other actions that are indicative of emotions or reactions to an external stimulus. A person might wrinkle her nose in response to an unpleasant smell, smile in response to something she finds funny, and lower her brow in response to something invoking confusion or skepticism. Human emotions frequently result from external stimuli. On any given day, an individual encounters a wide variety of external stimuli including any combination of visual, aural, gustatory, tactile, and other types of stimuli. Alone or in combination, the stimuli can invoke strong cognitive states in the individual. An individual's reactions to the received stimuli provide insight into the thoughts and feelings of the individual. Furthermore, the individual's responses to the stimuli can have a profound impact on the cognitive states experienced by the individual, and on those cognitive states experienced by others nearby the individual. The cognitive states of an individual can vary widely, ranging from happiness to sadness, contentment to worry, and tranquility to excitement, to name only a very few possible states.

People routinely experience a variety of cognitive states while they travel. Some people travel from one location to another for financial reasons such as commuting to and from work or school; for personal reasons such as pleasure, relaxation or discovery; or for exercise; to name only a few. Other people who travel may be unwilling travelers, fleeing from war, famine, natural disasters, or economic displacement. The modes of transportation include ground transportation, water transportation, and air transportation. People choose a mode of transportation based on convenience, availability, cost, or the purpose of the travel.

People spend a tremendous amount of time traveling. Whether waiting for a vehicle, traveling in the vehicle, attempting to park the vehicle, waiting in security lines to get on a vehicle, among many other travel related activities, substantial portions of time are committed to vehicular travel. Traveling in a vehicle is time consuming at best, and at worst, boring, frustrating, and irritating. Travel time can be time lost from productive activities such as work, study, art, and so on. Rush hour traffic, accidents, and poorly maintained roads complicate vehicle transportation. The difficulties of transportation can be exacerbated by operating an unfamiliar vehicle, traveling in an unfamiliar city, and even in some situations having to remember to drive on the opposite side of the road. Failure to address these transportation realities can have catastrophic consequences. Irritated operators of vehicles can experience road rage and other antisocial behaviors, while bored, sleepy, impaired, distracted, or inattentive drivers can cause vehicular accidents resulting in injury to themselves or other vehicle occupants, pedestrians, bicyclists, and/or animals, and damage to property.

SUMMARY

Vehicular manipulation uses cognitive state evaluation for vehicle navigation. The vehicle to be manipulated can be an autonomous vehicle, a semi-autonomous vehicle, and so on. An in-vehicle camera is used to obtain images of a first occupant of a first vehicle. The occupant can be the operator of the vehicle, a custodial driver of the vehicle, a passenger in the vehicle, and so on. The cognitive state data can include image data, facial data, etc. Other in-vehicle sensors can include a microphone for collecting voice data or audio data, or sensors to collect physiological data. A first computing device is used to analyze the one or more images to determine cognitive state data for the first occupant. The first computing device can be located within the first vehicle or beyond the first vehicle. A set of layers and weights is learned based on the cognitive state data. The set of layers and weights can be learned by a neural network such as a deep neural network, a convolutional neural network, a recursive neural network, etc. One or more images of a second occupant of a second vehicle are collected using an imaging device. The second vehicle can be the same vehicle, a second vehicle, a vehicle from a fleet of vehicles, and so on. The imaging device can be the first imaging device or another imaging device. The one or more images of the second occupant are analyzed to determine additional cognitive state data. The second vehicle is manipulated based on the additional cognitive state data that was analyzed using the set of layers and weights that were learned.

Disclosed embodiments provide techniques for vehicle manipulation using cognitive state evaluation for vehicle navigation, based on a computing device for analysis and learning. Further disclosed embodiments provide techniques for learning layers and weights for a neural network. The computing device can implement a neural network such as a deep neural network, a convolutional neural network, or a recursive neural network, based on the learned layers and weights. The neural network includes multiple layers that comprise one or more input layers, output layers, convolutional layers, and hidden layers. The learning is based on obtaining images including facial data of a first occupant of a first vehicle, and analyzing those images for cognitive state data for the first occupant. Further images are collected from a second occupant of a second vehicle. The further images are analyzed to determine additional cognitive state data. The second vehicle is manipulated based on the additional cognitive state data and the learned layers and weights. The evaluating of the images can include analyzing pixels within the images to identify a facial portion, and identifying a facial expression based on the facial portion. The second vehicle that is manipulated can be an autonomous vehicle or a semi-autonomous vehicle.

A computer-implemented method for vehicle manipulation comprises: obtaining one or more images of a first occupant of a first vehicle using a first imaging device within the first vehicle, wherein the one or more images include facial data of the first occupant; analyzing, using a first computing device, the one or more images to determine cognitive state data for the first occupant; learning a set of layers and weights based on the cognitive state data; collecting one or more images of a second occupant of a second vehicle, wherein the one or more images of the second occupant are analyzed to determine additional cognitive state data; and manipulating the second vehicle based on the additional cognitive state data that was analyzed using the set of layers and weights that were learned. The manipulating includes passing control from the custodial driver to the semiautonomous second vehicle or to the autonomous vehicle based on the additional cognitive state data. The one or more images that were obtained and the one or more images that were collected are from a single vehicle trip, or from two or more vehicle trips.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
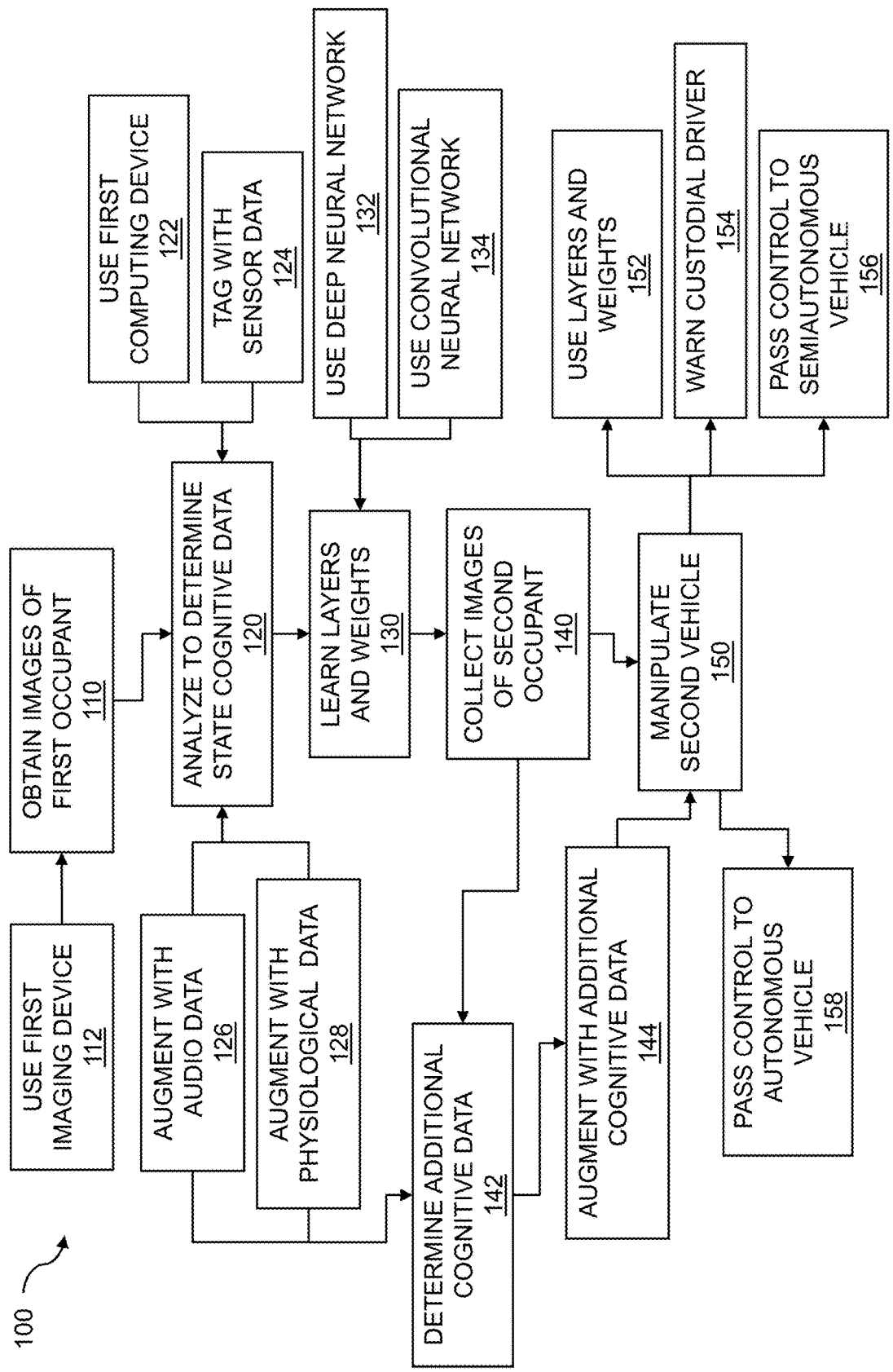
FIG. 1 is a flow diagram for cognitive state evaluation for vehicle navigation.

Cognitive analysis is a highly complex undertaking. The advent of computation techniques such as neural networks has enabled the implementation of the many tasks associated with cognitive analysis. Understanding and evaluating cognitive states including moods, emotions, or mental states, require a detailed and nuanced evaluation of facial expressions or other cues that people generate. The facial expressions or other cues are often generated subconsciously as a result of external stimuli. Techniques for image processing, and resulting vehicle manipulation and navigation using a neural network, are described herein. Image processing is a computational element critical to cognitive state analysis. Cognitive state analysis is important in many areas of human enterprise. The understanding of cognitive states can be used in a variety of fields, such as improving marketing analysis, assessing the effectiveness of customer service and retail experiences, and evaluating the consumption of content such as movies and videos. Further, understanding of cognitive states can be applied to manipulation of autonomous or semi-autonomous vehicles. By understanding the one or more cognitive states being experienced by an occupant of a vehicle, and the cognitive states being experienced by other occupants, including those occupants of other vehicles, a variety of vehicle manipulation steps can be taken. For example, if a vehicle occupant such as a custodial or "safety" driver is drowsy, inattentive, distracted, or impaired, control of an autonomous or semi-autonomous vehicle can be transferred to the vehicle from the occupant. Further, a recommendation can be made that the occupant take a break from operating a vehicle to rest, to have a meal, and the like.

The transfer of control to a semiautonomous or autonomous vehicle from an inattentive, distracted, or otherwise ineffective custodial driver to the vehicle can be performed for a variety of very important safety reasons. While a distracted driver can be annoyance to other vehicle operators due to swerving, erratic vehicle operation, or other antisocial behaviors, that same distracted driver can be a serious menace to people, animals, and property. The inattentive custodial driver who fails to see a vehicle swerve into the travel lane of the semiautonomous or autonomous vehicle can cause a serious accident. Similarly, the inattentive custodial driver who is not looking in the direction of travel and fails to see a person or animal in the road ahead can cause serious injury or death. By identifying problematic cognitive states in vehicle operators, the vehicles can be manipulated to maintain safe operation.

In embodiments, a computing device is used for analyzing images obtained using imaging devices. The analyzing includes cognitive state evaluation of occupants of vehicles. The imaging devices obtain images of one or more occupants of one or more vehicles. The results of the image analysis and processing is vehicle navigation. An imaging device within a first vehicle is used to obtain one or more images of an occupant of the first vehicle. A computing device is used to analyzed the images, including facial data, to determine cognitive state data for the occupant. The images can include images of a vehicle operator, one or more vehicle passengers, and so on. A set of layers and weights is learned based on the cognitive state data. The layers and weights comprise a neural network such as a deep neural network, a convolutional neural network, and so on. The neural network comprises multiple layers that include one or more input layers and output layers, one or more convolutional layers, and one or more hidden layers. The neural network can include a pooling layer, a bottleneck layer, etc. A pooling layer can be an average pooling layer, a max pooling layer, or other type of pooling layer. The cognitive states that can be determined by the analysis can include one or more of drowsiness, fatigue, distraction, impairment, fear, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Further images are evaluated using the multilayered analysis engine. The further images including further facial image data are collected for a second occupant of a second vehicle. The second vehicle is manipulated based on the additional cognitive state data that was analyzed using the set of layers and weights that were learned. The second vehicle can be an autonomous vehicle or a semi-autonomous vehicle. Audio data and physiological data can be collected and used to augment the cognitive state data. The manipulating includes passing control from the custodial driver to the semiautonomous second vehicle or the autonomous second vehicle based on the additional cognitive state data.

Referring now to the figures, FIG. 1 is a flow diagram for cognitive state evaluation for vehicle navigation. A first in-vehicle imaging device is used for obtaining one or more images of a first occupant of a first vehicle. The images can include facial data of the first occupant. A computing device is used for analyzing the one or more images to determine cognitive state data for the first occupant. A set of layers and weights is learned based on the cognitive state data. Images of a second occupant of a second vehicle are collected, where the one or more images of the second occupant are analyzed to determine additional cognitive state data. The second vehicle is manipulated based on the additional cognitive state data that was analyzed using the set of layers and weights that were learned.

The flow 100 includes obtaining one or more images of a first occupant 110 of a first vehicle using a first imaging device 112 with the first vehicle, where the one or more images include facial data of the first occupant. The images can include still images, frames from a video, and so on. The images can include visible light images, infrared images, and the like. The imaging device 112 can include any of a variety of cameras, where the cameras can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The first vehicle can include an automobile, a van, a sport utility vehicle (SUV), a truck, a bus, etc. The occupant of the first vehicle can be a passenger within the vehicle. More than one passenger may be present in the vehicle. In embodiments, the occupant can be a driver, an operator, a custodial driver, etc., within the vehicle. A custodial driver is a vehicle occupant to can take over operation of a vehicle such as a semiautonomous vehicle, an autonomous vehicle, etc.

The flow 100 includes analyzing 120, using a first computing device 122, the one or more images to determine cognitive state data for the first occupant. The first computing device can be located within or beyond the first vehicle. The first computing device can include one or more processors. The computing device can include a server such as a local server, a blade server, a remote server, a cloud server, a mesh server, a distributed server, and the like. The computing device can include a handheld computing device such as a smartphone, a tablet computer, etc. The cognitive state data can be based on the facial data or other data. In embodiments, the cognitive state data is indicative of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The analyzing can also determine mental states, emotional states, moods, etc. Further embodiments include tagging the cognitive state data with sensor data 124. The sensor data can include vehicle status data, meteorological data, and so on. In embodiments, the sensor data can include one or more of vehicle temperature, outside temperature, time of day, level of daylight, weather conditions, headlight activation, windshield wiper activation, entertainment center selection, entertainment center volume, etc.

The flow 100 further includes augmenting the cognitive state data based on audio data 126 collected on the first occupant. The audio data can include audio data collected within the vehicle such as cabin noise, music, etc., audio data collected outside the vehicle such as wind noise, road noise, traffic noise, etc., and other audio data. The audio data can include voices of one or more occupants of the vehicle. In embodiments, the audio information can include speech, where the speech can include speech of the occupant of the vehicle, a conversation between occupants, speech from an audio source such as a radio, a podcast, an audio book, etc. In embodiments, the audio information can include non-speech vocalizations. The non-speech vocalizations can include a range of human-generated sounds such as grunts, yelps, squeals, snoring, sighs, laughter, filled pauses, unfilled pauses, yawns, and the like. The flow 100 further includes augmenting the additional cognitive state data based on physiological data collected on the first occupant 128. Various types of physiological data can be collected such as "vital signs", position or attitude of the body of the occupant, and so on. In embodiments, the physiological data can include skin conductance or galvanic skin response, heartrate, heartrate variability, or respiratory rate, etc.

The flow 100 includes learning a set of layers and weights 130 based on the cognitive state data. The set of layers and weights can be used by a neural network (NN) to identify cognitive states, mental states, emotional states, moods, etc., of the occupant of the vehicle. Further, the layers and weights can be learned by the neural network. The layers and weights can be learned by various configurations of neural networks. In embodiments, the learning can be performed using a deep neural network 132 (DNN). The deep neural network can include input layers, output layers, hidden layers, etc. In embodiments, the learning can be performed using a convolutional neural network 134 (CNN). The convolutional neural network can include a feed-forward deep neural network. A convolutional neural network, for example, can include an input layer, a convolutional layer, a pooling layer, a rectified linear units (ReLU) layer, a classification layer, an output layer, and so on. In embodiments, a layer from the multiple layers can be fully connected. In further embodiments, the neural network can include a recursive neural network (RNN).

The flow 100 includes collecting one or more images of a second occupant 140 of a second vehicle. In embodiments, the first occupant and the second occupant are the same occupant. The first occupant and the second occupant can be different occupants such as a driver and passenger, two passengers, a passenger and a custodial driver, and the like. In embodiments, the first vehicle and the second vehicle can be the same vehicle. The first vehicle and the second vehicle can be traveling in the same travel lane, in adjacent travel lanes, in opposite travel lanes, etc. The one or more images can be collected using the first imaging device, a second imaging device, and so on. The images can include cognitive state data, audio data, physiological data, and the like. In embodiments, the one or more images that were obtained and the one or more images that were collected are from a single vehicle trip. The images that were obtained or collected can be analyzed for vehicle navigation during the trip. In other embodiments, the one or more images that were obtained and the one or more images that were collected are from two or more vehicle trips. The images from the two or more vehicle trips can be used to identify trends for vehicle manipulation that can be based on traffic patterns, road conditions such as detours or construction, and the like. In embodiments, the second vehicle can be an autonomous or semiautonomous vehicle. The autonomous or semiautonomous vehicle can include an automobile, a van, an SUV, a truck, a bus, etc. In embodiments, the second occupant can be the driver of the second vehicle. The second occupant could be an operator or a pilot of the second vehicle. In other embodiments, the second occupant can be a passenger of the second vehicle. The second vehicle can be a taxi cab, a peer-to-peer ridesharing service such as Uber™, an on-demand service such as Lyft™, and so on. In further embodiments, the second occupant can be a custodial driver of the second vehicle. The custodial driver, sometimes called a safety driver, can verify, test, operate, or otherwise oversee operation of the second vehicle. In embodiments, the custodial driver can perform supervision over an autonomous or semiautonomous vehicle.

In the flow 100, the one or more images of the second occupant are analyzed 142 to determine additional cognitive state data. As for the first occupant of the first vehicle, the additional cognitive state data can be indicative of drowsiness, fatigue, distraction, impairment, delight, excitement, and so on. The additional cognitive state data can be augmented with images, audio data, physiological data, etc. Embodiments can include augmenting the additional cognitive state data based on images from one or more additional vehicle occupants of the second vehicle. The second vehicle can be a car. The additional images can be collected using the first imaging device, a second imaging device, and so on. The flow 100 further includes augmenting the additional cognitive state data 144 based on audio data collected on the second occupant. The audio data collected on the second occupant can include speech data, non-speech vocalizations such as grunts, yelps, squeals, snoring, and the like. Other cognitive state data can be used for the augmenting. Further embodiments can include augmenting the additional cognitive state data based on physiological data collected on the second occupant. Various types of physiological data can be collected from the second occupant. In embodiments, the physiological data can include skin conductance or galvanic skin response, heartrate, heartrate variability, or respiratory rate, and so on.

The flow 100 includes manipulating the second vehicle 150 based on the additional cognitive state data that was analyzed. The analyzing of the cognitive state data can be performed by a neural network such as a deep neural network, convolutional neural network, recursive neural network, etc., using the set of layers and weights 152 that were learned. The manipulating the second vehicle can include setting an alert such as a flashing light or a sound, applying brakes, performing an evasive maneuver, and so on. The manipulation can also be based on other events such as traffic event, a person or animal present in the travel lane of the first or second vehicle, a road hazard, etc. In embodiments, the manipulating includes warning the custodial driver 154 when the additional cognitive state data indicates inattentiveness. The inattentiveness can refer to the cognitive state of the occupant of the first vehicle such as a distracted driver, the cognitive state of the custodial driver, etc. The warning to the custodial driver can include a display such as a warning light, a heads up display, an alarm such as a buzzer, chime, or bell, and so on. In the flow 100, the manipulating can include passing control from the custodial driver to the semiautonomous second vehicle 156 based on the additional cognitive state data. The passing control to the semiautonomous second vehicle can include enabling the semiautonomous vehicle to apply brakes, to sound an alarm such as a horn, to flash lights such as headlights, to perform an evasive maneuver such as steering into another travel lane, and the like. Further to the flow 100, the manipulating can include passing control from the custodial driver to the autonomous second vehicle 158 based on the additional cognitive state data. The manipulating can be augmented. Further embodiments include augmenting the manipulating based on the additional cognitive state data that was augmented. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors. Various embodiments of the flow 100, or portions thereof, can be included on a semiconductor chip and implemented in special purpose logic, programmable logic, and so on.

Figure 2:
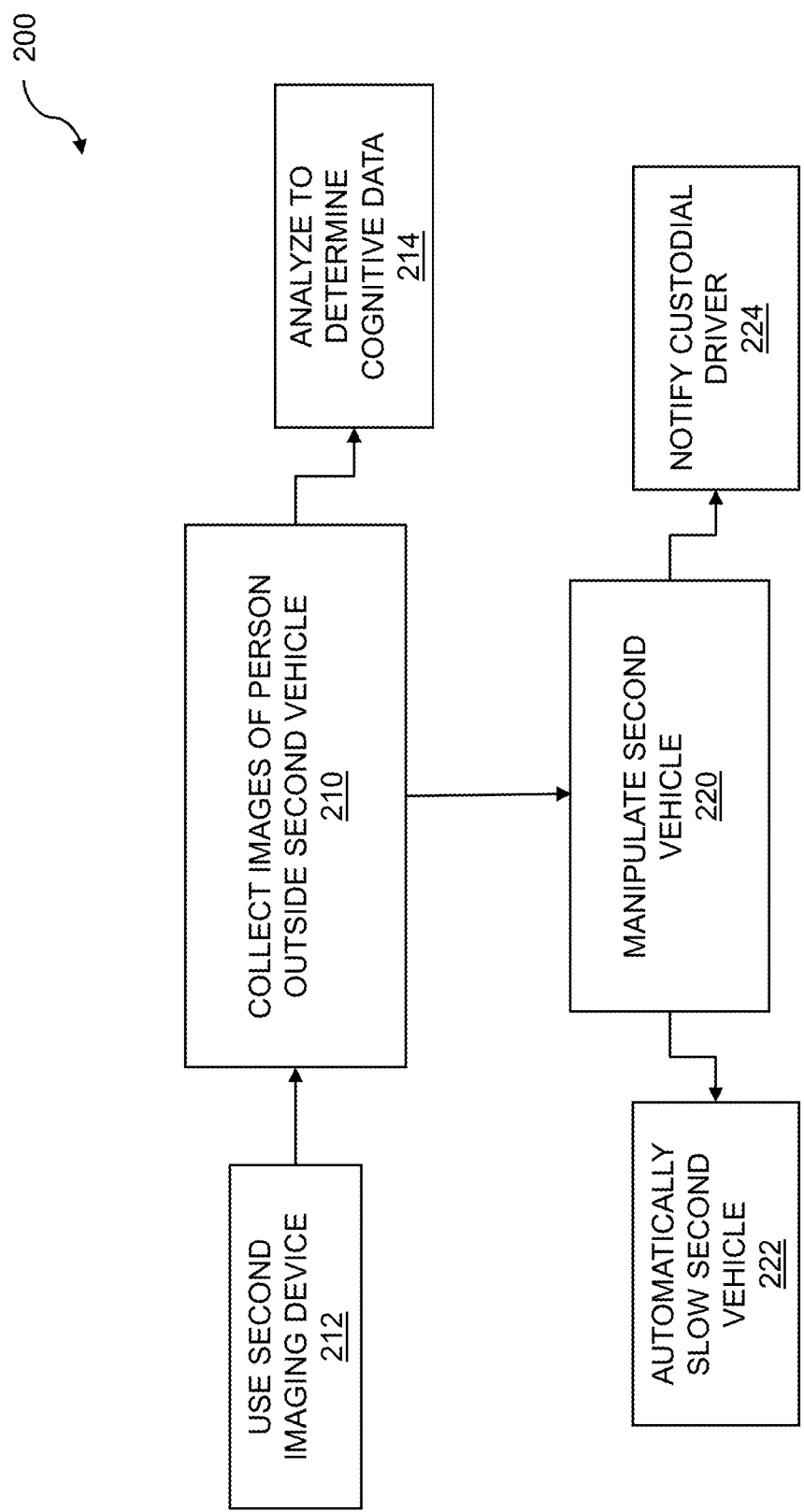
FIG. 2 is a flow diagram for second image device use.

FIG. 2 is a flow diagram for second imaging device use. Vehicle navigation is based on cognitive state evaluation of occupants of vehicles. An imaging device such as a camera is used to obtain images of an occupant of a first vehicle. The images can include data such as facial data of the occupant of the first vehicle. A computing device is used to analyze the images to determine cognitive state data for the occupant. A set of layers and weights is learned, such as layers and weights that can be used by a neural network, based on the cognitive state data. A second imaging device, such as a second camera, can be used for collecting one or more images of a second occupant of a second vehicle. The images of the second occupant are analyzed to determine additional cognitive state data. The second vehicle is manipulated based on the additional cognitive state data. The flow 200 includes collecting images of a person outside of the second vehicle 210. The person outside of the second vehicle can be adjacent to the second vehicle or at a distance from the second vehicle. The person outside the second vehicle can be traveling in the same direction as the second vehicle, crossing ahead of the second vehicle, etc. In embodiments, the person outside of the second vehicle can be a pedestrian. The pedestrian can be traveling in the direction of travel of the second vehicle, traveling in an opposite direction, traveling in a crosswalk, traveling outside of a crosswalk, etc. In some embodiments, the person outside the vehicle is a child. In embodiments, the person outside of the second vehicle can be operating a human-powered transportation device. The person can be operating a variety of human-powered transportation devices such as a bicycle, a tricycle, or a rickshaw, a velomobile, etc. In other embodiments, the human-powered transportation device is a skateboard, longboard, scooter, roller skis, skates, and the like.

The flow 200 continues. The images of the person outside the second vehicle can be collected using a second imaging device 212, where the second imaging device can include a camera, a video camera, or other device suitable for capturing images that can be digitally analyzed. The second imaging device can be a forward-facing camera mounted to the vehicle. In embodiments, other imaging devices can be mounted to the vehicle and can include side-facing devices, rear-facing devices, ground facing or scanning devices, upward-facing devices, and so on. The imaging device can detect nonvisible light spectra such as infrared spectra. In embodiments, the images of a person outside of the second vehicle can include facial images of the person. The facial images can include a full facial image, a three-quarters facial image, a profile facial image, a one-quarter facial image, etc. In other embodiments, the images of a person outside of the second vehicle can include body posture images of the person. The body posture images can include upright, slouching, hunched, huddled, reclining, etc. In the flow 200, the images of the person outside of the second vehicle are analyzed to determine cognitive state data 214 for the person outside of the second vehicle. The cognitive state data can be indicative of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

The flow 200 further includes manipulating the second vehicle 220 based on the cognitive state date for the person outside of the second vehicle. The manipulating the second vehicle can include can include actions, processes, techniques, and so on. The manipulating can include flashing headlights, sounding an alert such as a horn, performing an evasive maneuver, and so on. In a usage example, the person outside the second vehicle can be a pedestrian with a cognitive state of attention while that person is walking on a sidewalk adjacent to a travel lane of the second vehicle. For this example, the manipulating the second vehicle can include manipulations such as shifting to a lane farther from the person or perhaps taking no action. In another usage example, the person outside the second vehicle can be a pedestrian with a cognitive state of distraction while that person is walking within the travel lane of the second vehicle and outside a marked crosswalk. For this latter example, the manipulating the second vehicle can include sounding an alert such as a horn, a hard application of brakes, an evasive maneuver, and so on. In embodiments, the manipulating can include automatically slowing the second vehicle 222. The slowing can be performed due to traffic patterns, road hazards such as debris or pavement gaps, people or animals in the travel lane, etc. The slowing the second vehicle can range from a minor adjustment of vehicle speed to emergency braking as described in a usage example. In embodiments, the further manipulating can include notifying a custodial driver 224 of the second vehicle. If the second vehicle is an autonomous vehicle, a semiautonomous vehicle, or the like, then the vehicle can have an occupant who is responsible for overseeing and ensuring safe operation of the vehicle. The occupant can be a custodial driver, also called a safety driver, who can take over the autonomous or semiautonomous vehicle to perform an emergency maneuver, provide a vehicle operation correction, and the like. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors. Various embodiments of the flow 200, or portions thereof, can be included on a semiconductor chip and implemented in special purpose logic, programmable logic, and so on.

Figure 3:
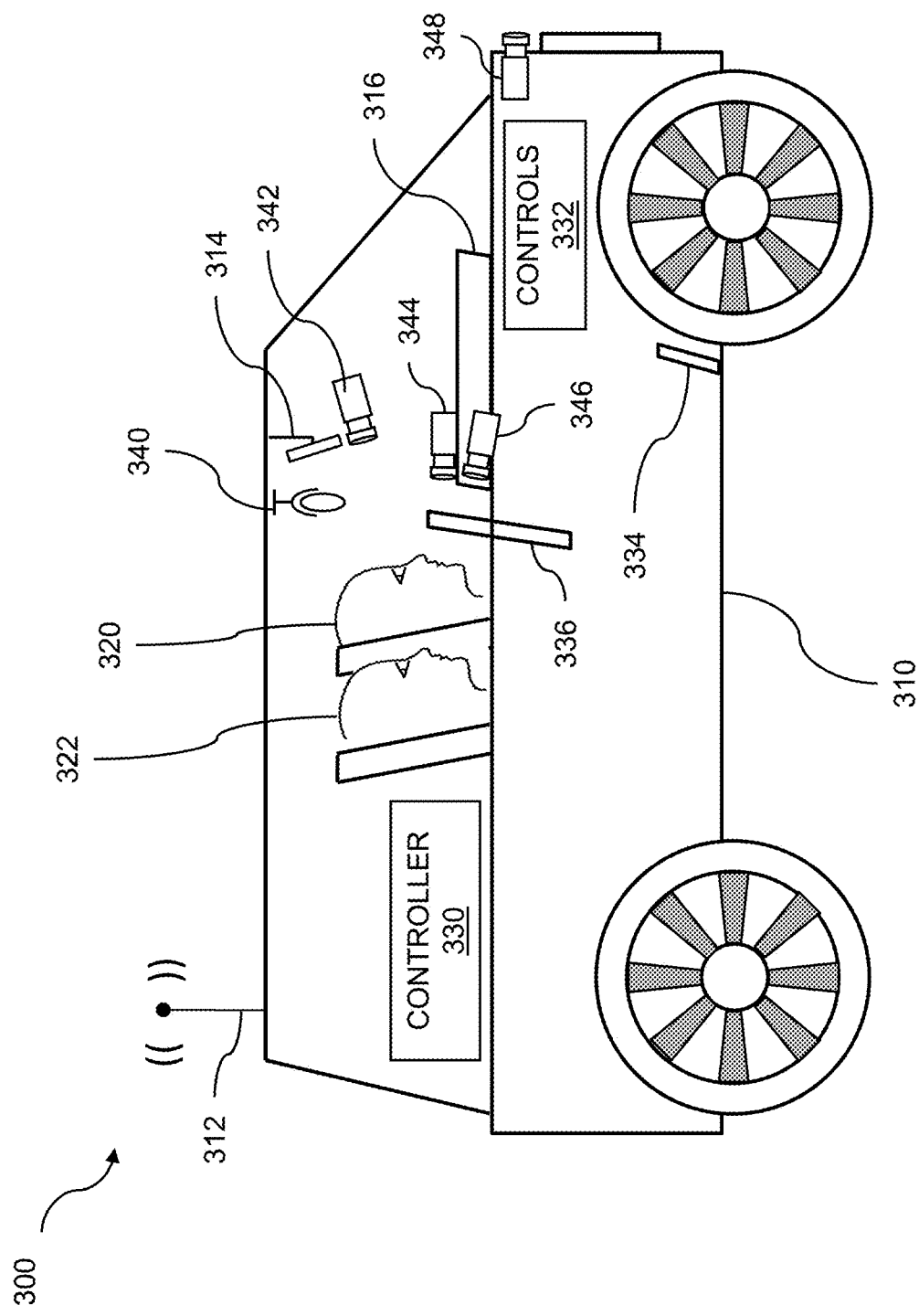
FIG. 3 is a system diagram for an interior of a vehicle.

FIG. 3 is a system diagram for an interior of a vehicle 300. Vehicle navigation can use cognitive state evaluation for vehicle manipulation. Images including facial data are obtained of an occupant of a first vehicle using an imaging device such as a camera. A computing device is used to analyze the images to determine cognitive state data. A set of layers and weights are learned based on the cognitive state data. Images of an occupant of a second vehicle are obtained and analyzed to determine additional cognitive state data. The second vehicle is manipulated based on the additional cognitive state data which is analyzed using the set of layers and weights. One or more occupants of a vehicle 310, such as occupants 320 and 322, can be observed using a microphone 340, one or more cameras 342, 344, or 346, and other audio and image capture techniques. The image data can include video data. The video data and the audio data can include cognitive state data, where the cognitive state data can include facial data, voice data, physiological data, and the like. The occupant can be a driver occupant 320 of the vehicle 310, a passenger occupant 322 within the vehicle, and so on. In embodiments, the second occupant 322 can be a custodial driver of the second vehicle. The custodial driver can operate the vehicle 310 or can take over operation of the vehicle. In embodiments, the custodial driver can perform supervision over an autonomous or semiautonomous vehicle. That is, if a driving event were to occur, such as another vehicle swerving into the travel lane of the vehicle 310, a pedestrian or bicyclist present in the travel lane, an animal darting into the travel lane, and so on, then the custodial driver could take over the autonomous or semiautonomous vehicle to perform an emergency maneuver or other appropriate maneuver.

The cameras or imaging devices that can be used to obtain images including facial data from the occupants of the vehicle 310 can be positioned to capture the face of the vehicle operator, the face of a vehicle passenger, the face of the custodial driver, multiple views of the faces of occupants of the vehicle, and so on. The cameras can be located near a rear-view mirror 314, such as camera 342, positioned near or on a dashboard 316, such as camera 344, positioned within the dashboard, such as camera 346, and so on. In embodiments, one or more cameras can be positioned to capture images outside of the vehicle 310. A camera 348 can be positioned so as to capture images ahead of the vehicle such as the travel lane, other vehicles, road hazards, and so on. The camera 348 also can be used to capture images of driving events as described elsewhere. The microphone, or audio capture device, 340 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 310 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 310 can include standard controls such as a steering wheel 336, a throttle control (not shown), a brake 334, and so on. The interior of the vehicle can include other controls 332 such as controls for seats, mirrors, climate controls, audio systems, etc. The controls 332 of the vehicle 310 can be controlled by a controller 330. The controller 330 can control the vehicle 310 in various manners such as autonomously, semi-autonomously, assertively to a vehicle occupant 320 or 322, etc. In embodiments, the controller provides vehicle control techniques, assistance, etc. The controller 330 can receive instructions via an antenna 312 or using other wireless techniques. The controller 330 can be preprogrammed to cause the vehicle to follow a specific route. The specific route that the vehicle is programmed to follow can be based on the cognitive state of the vehicle occupant. The specific route can be chosen based on lowest stress, least traffic, best view, shortest route, and so on.

Figure 4:
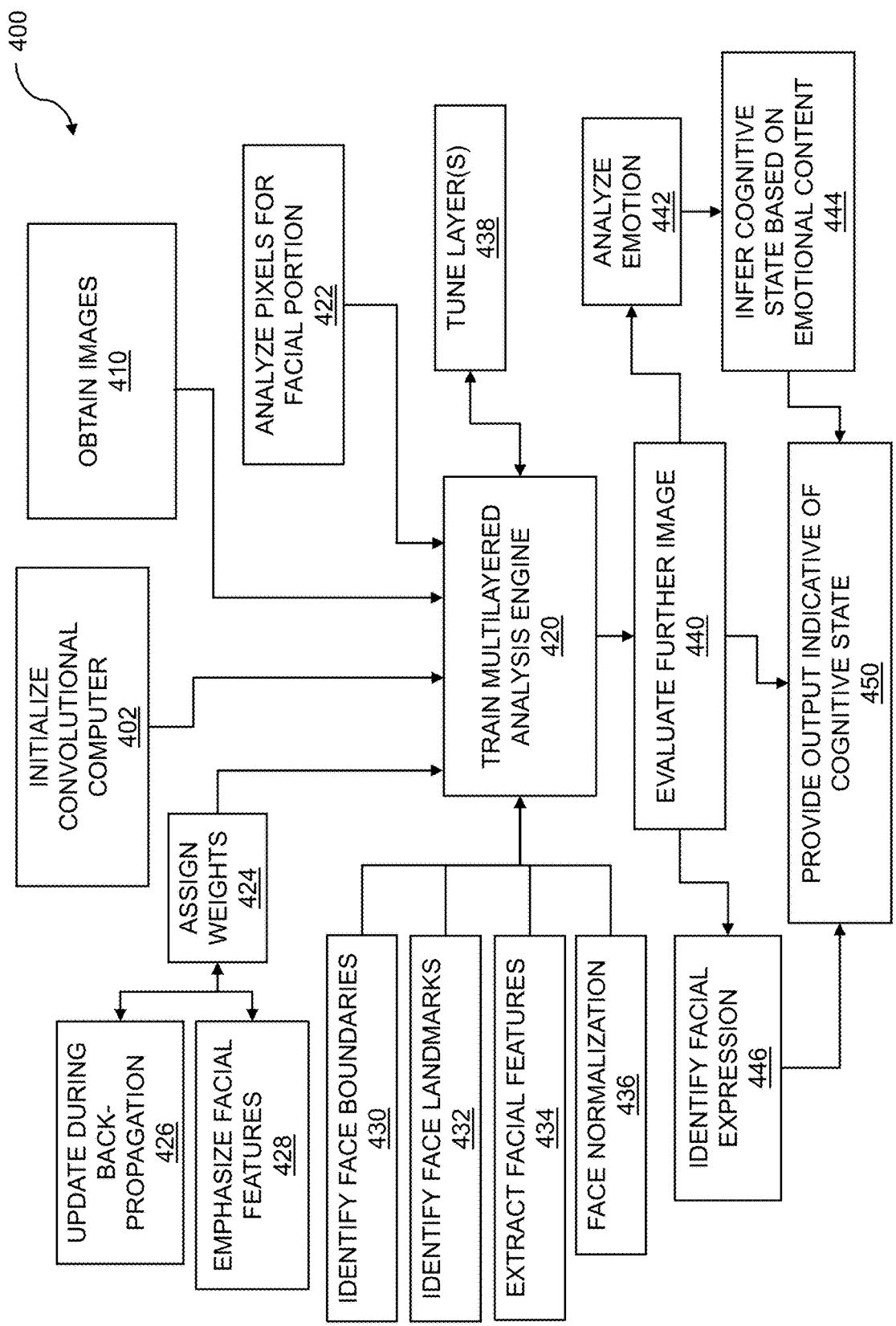
FIG. 4 is a flow diagram representing deep convolutional processing image analysis.

FIG. 4 is a flow diagram representing deep convolutional processing image analysis. Convolutional image processing can be used for vehicle manipulation, vehicle navigation, and so on. Images of an occupant of a first vehicle are obtained. The images, including facial data, are analyzed for cognitive state data. Layers and weights are learned. Images of a second occupant of a second vehicle are collected and analyzed for additional cognitive state data. The second vehicle is manipulated based on the additional cognitive state data that was analyzed using the layers and weights.

The flow 400 shows a computer-implemented method for image analysis. The flow 400 includes initializing a convolutional computer 402. A convolutional computer can either be specialized hardware designed specifically for neural network convolution, or it can comprise unique software that enables a generic computer to operate as a specialized convolutional machine. The convolutional computer may exist as dedicated hardware, or it may exist as part of a networked structure, such as a supercomputer, a supercomputer cluster, a cloud-based system, a server-based system, a distributed computer network, and the like. The flow 400 includes obtaining a plurality of images 410. Each of the plurality of images can include at least one human face. In embodiments, each image includes metadata. The metadata can include information about each face that is entered by human coders. The metadata can include a perceived facial expression and/or cognitive state. The metadata can further include demographic information such as an age range, gender, and/or ethnicity information. Since different demographic groups might register emotions in different ways, the demographic information can be used to further enhance the output results of the multilayered analysis engine. For example, some demographic groups might not smile as frequently or as intensely as others. Thus, a compensation can be applied in these circumstances when analyzing smiles to effectively normalize the results. A similar approach can be applied to other facial expressions and/or cognitive states.

The flow 400 includes training a multilayered analysis engine 420 using the plurality of images, wherein the multilayered analysis engine includes multiple layers that include one or more convolutional layers and one or more hidden layers, and wherein the multilayered analysis engine is used for emotional analysis. Hidden layers are layers within the multilayered analysis engine with outputs that are not externally exposed. The output of hidden layers feeds another layer, but the output of the hidden layer is not directly observable. The training can include submitting multiple images to the multilayered analysis engine. In a supervised learning scenario, the multilayered analysis engine makes an assessment of the facial expression and/or cognitive state and compares its output to the human-coded assessment in the metadata. Various parameters such as weights between the layers can be adjusted until a majority of the input images are correctly classified by the multilayered analysis engine. Alternate embodiments can be implemented wherein stopping criteria is used. A desired target or accuracy is selected and images that have been labeled are analyzed. Once the target cognitive states or facial expressions identified by the neural network match those which have been labeled, then the learning can be stopped. In some cases, stopping criteria can be based on the number of images that are matched to the number of re-learning steps used, the decrease in error rates, the reduction of error rates to a predefined limit, the number of back propagation operations performed, and so on.

Thus, the flow 400 can further include assigning weights 424. The assignment of weights can be influenced by updating during back-propagation 426. Backpropagation can include calculation of a loss function gradient which is used to update the values of the weights as part of a supervised learning process. The assignment of weights can be selected to emphasize facial features 428, such as eyes, mouth, nose, eyelids, eyebrows, and/or chin. In other embodiments, the input images are not associated with metadata pertaining to facial expressions and/or cognitive states. In such cases, the multilayered analysis engine is trained using an unsupervised learning process.

The flow 400 includes evaluating a further image 440 using the multilayered analysis engine, wherein the evaluating includes analyzing pixels within the further image to identify a facial portion 422 and identifying a facial expression 446 based on the facial portion. The facial expression can include a smile, frown, laugh, expression of surprise, concern, confusion, and/or anger, among others. The analyzing of pixels for identifying a facial portion 422 can include identifying a face contour, as well as locating facial features such as eyes, nose, mouth, chin, and cheekbones. The further image 440 is a subject image that is to be analyzed by the multilayered analysis engine. Thus, once the multilayered analysis engine is trained, a subject image can be input to the multilayered analysis engine, and the multilayered analysis engine can analyze the subject image to identify a facial expression 446 and/or an output indicative of a cognitive state 450. A facial expression can correlate to more than one cognitive state, depending on the circumstances. For example, a smile can indicate happiness in many situations. However, in some cases, a person might smile while experiencing another cognitive state, like embarrassment. The "happy" smile might have slightly different attributes than the "embarrassed" smile. For example, the lip corners can be pulled higher in a "happy" smile than in an "embarrassed" smile. Through the training of the multilayered analysis engine 420, the multilayered analysis engine can learn the difference between the variants of a facial expression (e.g. smiles) to provide an output indicative of cognitive state 450.

The flow 400 includes analyzing an emotion 442. The emotion can be a representation of how the subject person is feeling at the time of image acquisition. The emotion analysis can be based on facial features and can include the use of action units (AUs). Such AUs can include, but are not limited to, brow lowerer, nose wrinkler, and mouth stretch, just to name a few. In practice, many more AUs can be examined during analyzing an emotion 442. The flow 400 includes inferring a cognitive state based on emotional content within a face associated with the facial portion 444. The emotional content can include, but is not limited to, facial expressions such as smiles, smirks, and frowns. Emotional content can also include actions such as lip biting, eye shifting, and head tilting. Furthermore, external features such as tears on a face can be part of the emotional content.

For example, detecting the presence of tears can be used in determining an expression/cognitive state of sorrow. However, in some instances, tears can also signify a cognitive state of extreme joy. The multilayered analysis engine can examine other factors in conjunction with the presence of tears to distinguish between the expressions of sorrow and joy.

The flow 400 includes tuning one or more layers 438 within the multiple layers for a particular cognitive state. In some embodiments, the tuning is for the last layer within the multiple layers where that last layer is tuned for identifying a particular cognitive state. In other embodiments, multiple layers are tuned. The multilayered analysis engine can include many layers. In embodiments, tuning the last layer is used to adjust the output so that the cognitive state and/or facial expressions provided by the multilayered analysis engine agree with the images used to train the multilayered analysis engine. For example, if images used for training contain facial expressions indicative of joy, but the output provided by the multilayered analysis engine is not indicating joy in a majority of the cases, then the last layer can be tuned so that the output provided by the multilayered analysis engine will indicate joy in a majority of the cases. The tuning can include adjusting weights, constants, or functions within and/or input to the last layer. Furthermore, other tuning techniques can be employed including learning from previous layers. In addition, later layers can be tuned to learn different expressions or further expressions so that other cognitive states or facial expressions are identified by the neural network.

The flow 400 includes identifying boundaries of the face 430. Identifying the existence of a face within an image can be accomplished in a variety of ways, including, but not limited to, utilizing a histogram-of-oriented-gradient (HoG) based object detectors. The flow 400 includes identifying landmarks of the face 432. The landmarks are points of interest within a face. These can include, but are not limited to, the right eye, left eye, nose base, and lip corners. The flow 400 includes extracting features of the face 434. The features can include, but are not limited to, eyes, eyebrows, eyelids, lips, lip corners, chin, cheeks, teeth, and dimples.

The flow 400 can include various types of face normalization 436 such as rotating, resizing, contrast adjustment, brightness adjustment, cropping, and so on. One or more of these normalization processes can be executed on faces within the plurality of images. The normalization steps can be performed on images, videos, or frames within a video. In embodiments, the image is rotated to a fixed orientation by an input layer of the multilayered analysis engine. For example, a face that is tilted at a 30-degree angle can be rotated such that it is oriented vertically, so that the mouth is directly below the nose of the face. In this way, the subsequent layers of the multilayered analysis engine work with a consistent image orientation.

As part of the training, the flow 400 includes training an emotion classifier for emotional content. The emotion classifier can include one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, shock, surprise, fear, curiosity, humor, sadness, poignancy, or mirth. In embodiments, the multilayered analysis engine is trained for a specific emotion such as shock. For example, in an application for determining the effectiveness of scary scenes in a horror movie, the multilayered analysis engine can be specifically trained to identify a facial expression of shock, corresponding to a cognitive state of surprise combined with fear. The horror movie is then shown to a test audience, where one or more cameras obtain images of the audience as the movie is being viewed. Facial images are acquired at a predetermined time after the presentation of a scary scene. The images can be acquired at a time ranging from about 300 milliseconds to about 700 milliseconds after presentation of the scary scene. This allows a viewer sufficient processing time to react to the scene, but is not so long that the viewer is no longer expressing their initial reaction.

In the flow 400, the training of the multilayered analysis engine comprises deep learning. Deep learning is a type of machine learning utilizing neural networks. In general, it is difficult for a computer to interpret the meaning of raw sensory input data, such as digital images that are represented as an array of pixels. Converting from an array or subset of pixels to identification of an object within the image, such as a human face, is very complicated. Direct evaluation of this mapping is computationally impractical to solve directly. However, embodiments disclosed herein comprise a multilayered analysis engine that utilizes deep learning. The multilayered analysis engine can determine features within an image by dividing the highly complex mapping into a series of more simple mappings, each processed by a different layer of the multilayered analysis engine. The input image is presented to an input layer, which performs initial processing on the image. Then one or more hidden layers extract features from the image. In embodiments, the outputs of the hidden layers are not directly observable. The hidden layers can provide evaluation of cognitive states or facial expressions without specific interpretation or labels being provided. The outputs of the hidden layers can, however, be used by further layers within the convolutional neural network to perform the cognitive state or facial expression analysis.

When an image is input to the multilayered analysis engine, the input layer can be used to identify edges by comparing the brightness of neighboring pixels or other edge detection process. The edges can then be input to a subsequent hidden layer, which can then extract features such as corners. The process continues with additional hidden layers, each additional layer performing additional operations, and culminating with an output layer that produces a result which includes a facial expression and/or cognitive state. Thus, the deep learning network provides an improved automated detection of facial expressions and/or cognitive states, enabling new and exciting applications such as large-scale evaluation of emotional response.

In the flow 400, the multilayered analysis engine comprises a convolutional neural network. Convolutional neural networks (CNNs) share many properties with ordinary neural networks. For example, they both include neurons that have learnable weights and biases. Each node/neuron receives some inputs and performs a function that determines if the node/neuron "fires" and generates an output. However, CNNs are well-suited for inputs that are images, allowing for certain optimizations to be incorporated into the architecture of the CNN. CNNs make the forward function more efficient to implement and they improve the performance of image analysis. The flow 400 further includes inferring a cognitive state based on emotional content within a face detected within the facial image data, wherein the cognitive state includes of one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 400 may be changed in order, repeated, omitted, or the like without departing from the disclosed concepts. Various embodiments of the flow 400 can be included in a computer program product embodied in a non-transitory computer readable medium that includes code executable by one or more processors. Various embodiments of the flow 400, or portions thereof, can be included on a semiconductor chip and implemented in special purpose logic, programmable logic, and so on.

Figure 5:
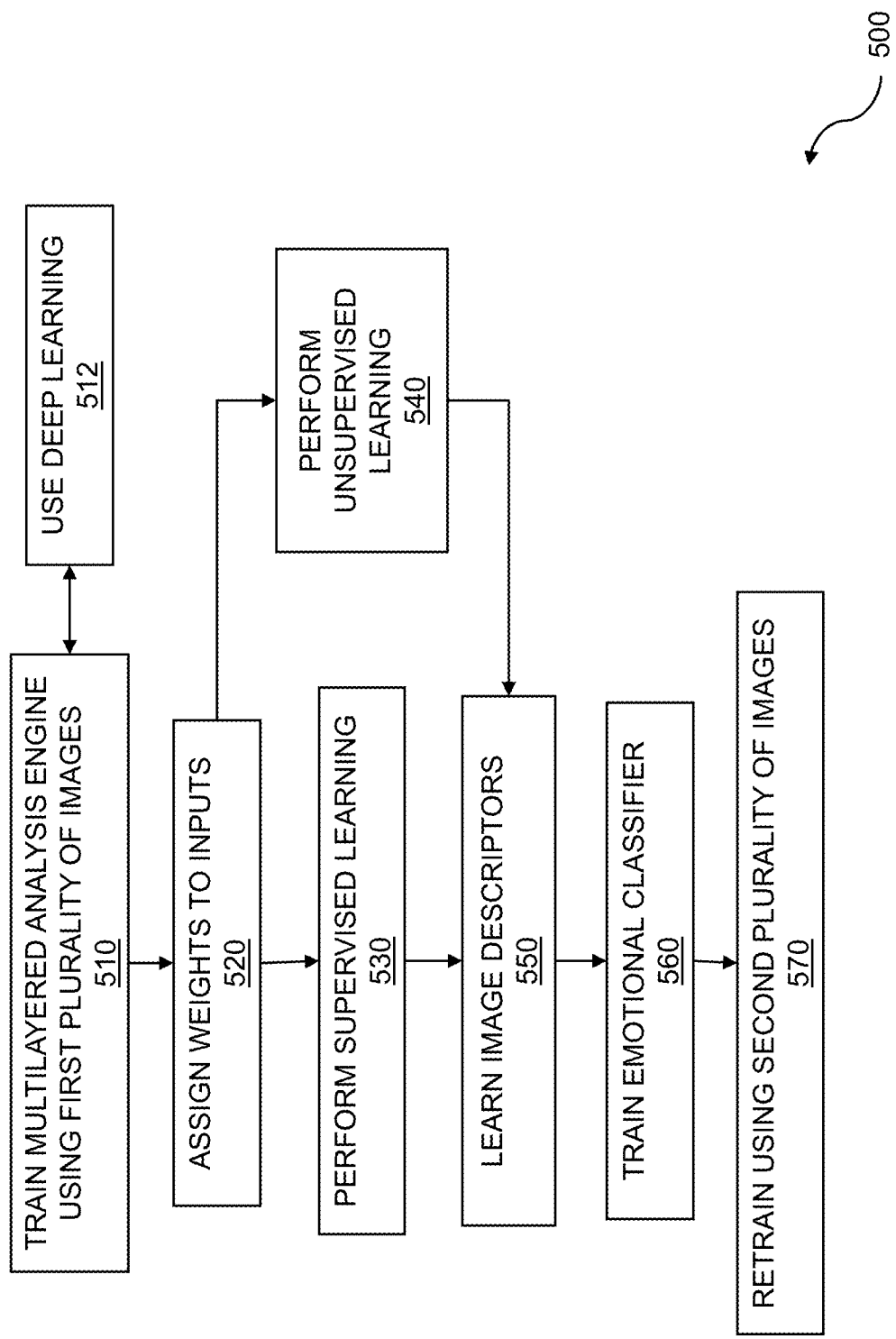
FIG. 5 is a flow diagram representing training.

FIG. 5 is a flow diagram representing training. A neural network such as a deep neural network, a convolutional neural network, a recursive neural network, and so on, can be trained for cognitive state evaluation. The cognitive state evaluation can be used for vehicle manipulation including vehicle navigation. Images including facial data are obtained using an imaging device. A computer analyzes the images for cognitive state data. A set of layers and weights is learned from the cognitive state data. Images of a second occupant of a second vehicle are collected and analyzed for additional cognitive state data. The second vehicle is manipulated based on the additional cognitive state data. The flow 500 includes training a multilayered analysis engine using a first plurality of images 510. The flow 500 includes assigning weights to inputs 520. The weights can be applied to inputs to the layers that comprise the multilayered analysis engine. In some embodiments, the weights are assigned an initial value that update during the training of the multilayered analysis engine based on processes such as backpropagation. In embodiments, the flow 500 includes performing supervised learning 530 as part of the training by using a set of images from the plurality of images that have been labeled for cognitive states. In other embodiments, the flow 500 includes performing unsupervised learning 540 as part of the training.

As part of the training, the flow 500 includes learning image descriptors 550 for emotional content. The image descriptors can include features within an image such as those represented by action units (AU). The descriptors can include, but are not limited to, features such as a raised eyebrow, a wink of one eye, or a smirk. In the flow 500, the image descriptors are identified based on a temporal co-occurrence with an external stimulus. The external stimulus can include media content such as an advertisement, a scene from a movie, or an audio clip. Additionally, the external stimulus can include a live event such as a siren, a thunder clap, or a flashing light that occurs in the room where the subject is located. The flow 500 includes training emotional classifiers 560. By analyzing multiple training images, the multilayered analysis engine can learn that lip corners pulled down in conjunction with lowered brows may be indicative of a cognitive state of disappointment. As more and more images are reviewed, the multilayered analysis engine generally becomes more proficient in analyzing cognitive state and/or facial expressions.

The flow 500 includes retraining the multilayered analysis engine using a second plurality of images 570. In some embodiments, once an initial training session has been completed, the retraining occurs using images of a specific subset of emotions. For example, the second plurality of images can focus exclusively on fear, shock, and surprise. The second plurality of images can be tailored to the emotions of interest for the users of the multilayered analysis engine. In the flow 500, the retraining updates weights on a subset of layers within the multilayered analysis engine. In embodiments, the subset of layers is a single layer within the multilayered analysis engine. Additionally, the flow 500 can include the use of deep learning 512 to accomplish the training. Various steps in the flow 500 may be changed in order, repeated, omitted, or the like without departing from the disclosed concepts. Various embodiments of the flow 500 can be included in a computer program product embodied in a non-transitory computer readable medium that includes code executable by one or more processors. Various embodiments of the flow 500, or portions thereof, can be included on a semiconductor chip and implemented in special purpose logic, programmable logic, and so on.

Figure 6:
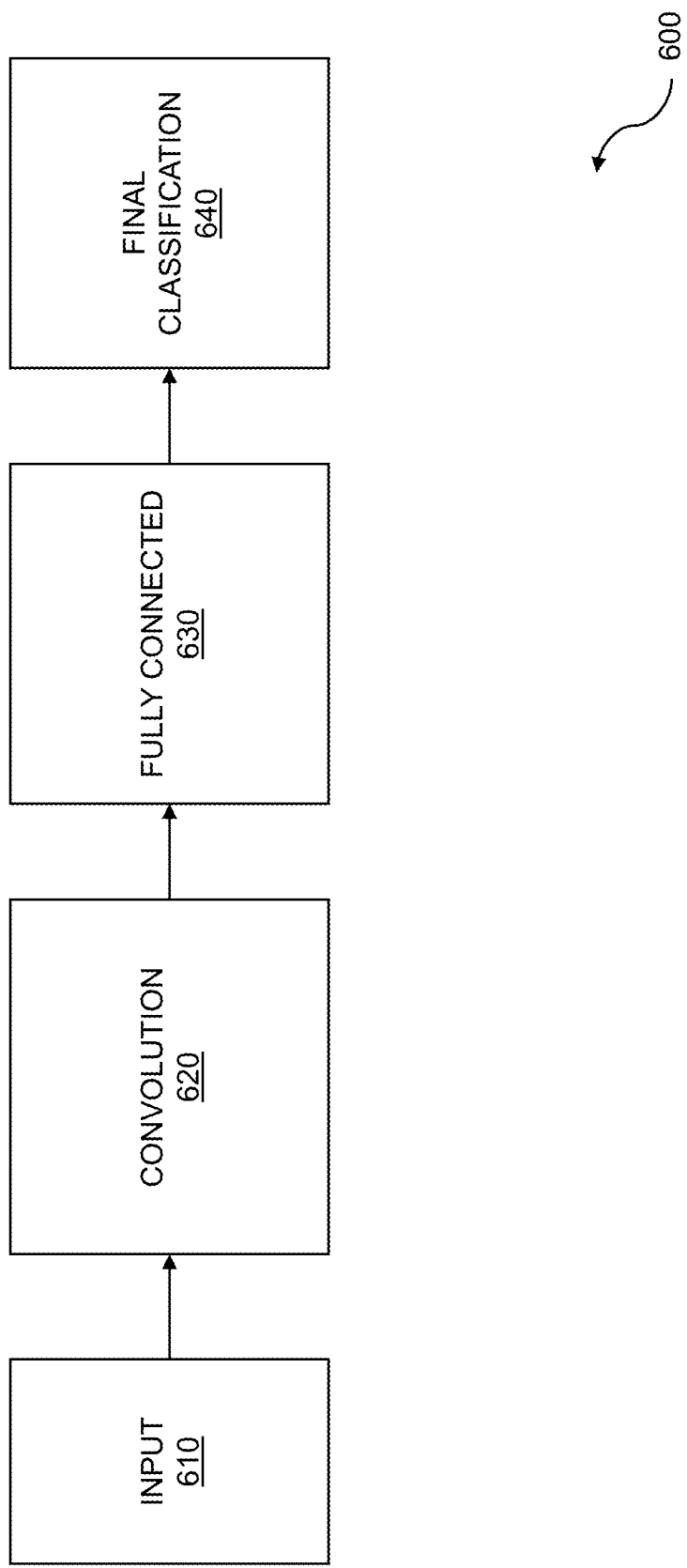
FIG. 6 is an example showing a pipeline for facial analysis layers.

FIG. 6 is an example 600 showing a pipeline for facial analysis layers. A pipeline of facial analysis layers can be applied to vehicle manipulation, including vehicle navigation, that uses cognitive state evaluation. The vehicle manipulation or navigation can use a neural network trained for cognitive state evaluation. Images of an occupant of a first vehicle are obtained by using an imaging device within the vehicle. The images which include facial data are analyzed for cognitive state data. Layers and weights are learned. Images of a second occupant of a second vehicle are collected and analyzed for additional cognitive state data. The second vehicle is manipulated based on the additional cognitive state data. The example 600 includes an input layer 610. The input layer 610 receives image data. The image data can be input in a variety of formats, such as JPEG, TIFF, BMP, and GIF. Compressed image formats can be decompressed into arrays of pixels, wherein each pixel can include an RGB tuple. The input layer 610 can then perform processing such as identifying boundaries of the face, identifying landmarks of the face, extracting features of the face, and/or rotating a face within the plurality of images. The output of the input layer can then be input to a convolution layer 620. The convolution layer 620 can represent a convolutional neural network and can contain a plurality of hidden layers. A layer from the multiple layers can be fully connected. The convolutional layer 620 can reduce the amount of data feeding into a fully connected layer 630. The fully connected layer processes each pixel/data point from the convolutional layer 620. A last layer within the multiple layers can provide output indicative of a certain cognitive state. The last layer is the final classification layer 640. The output of the final classification layer 640 can be indicative of the cognitive states of faces within the images that are provided to input layer 610.

Figure 7:
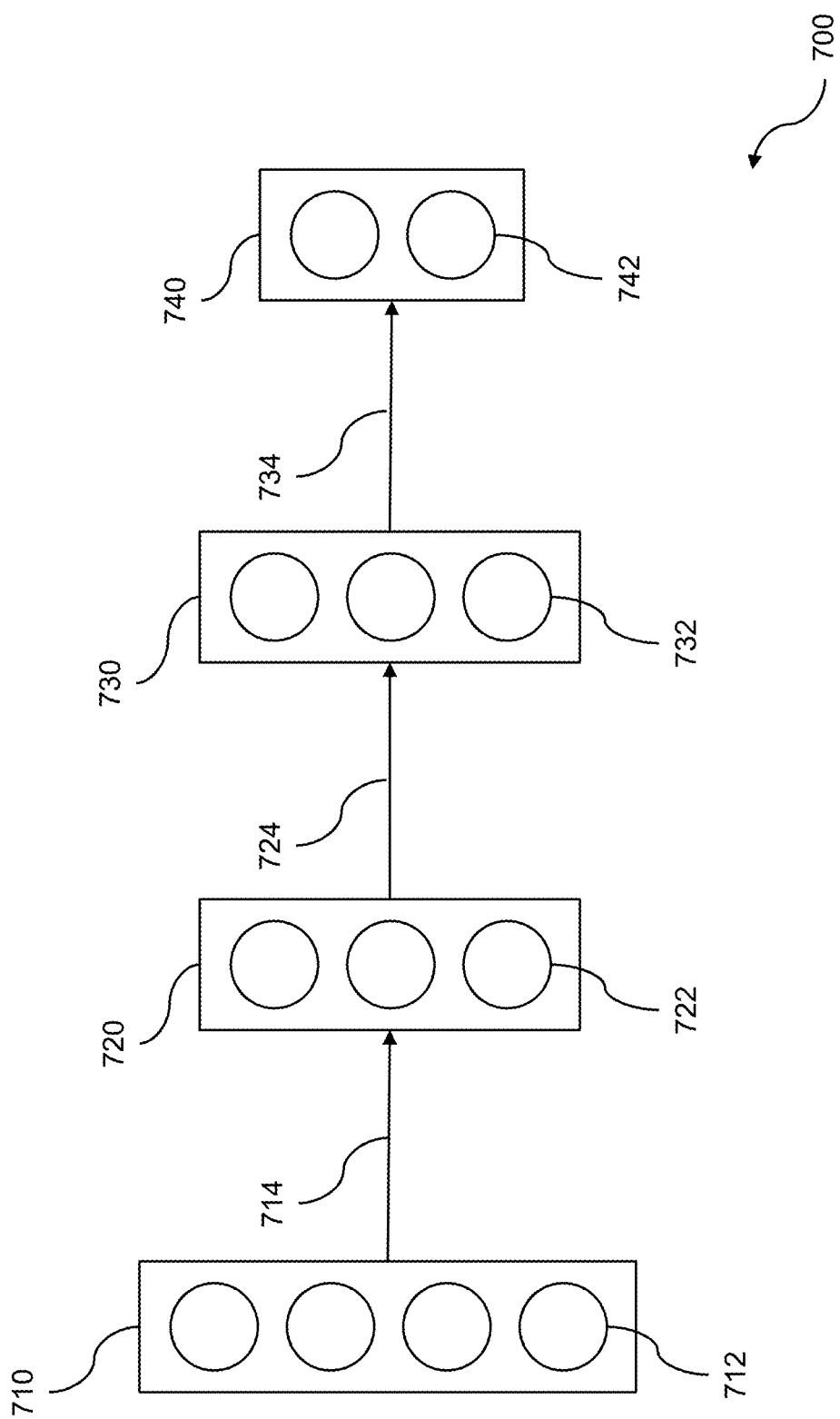
FIG. 7 is an example illustrating a deep network for facial expression parsing.

FIG. 7 is an example 700 illustrating a deep network for facial expression parsing. Facial expression parsing can be applied to vehicle manipulation or navigation. Vehicle navigation uses cognitive state evaluation. Images including facial data of a vehicle occupant are obtained and analyzed for cognitive state data. Layers and weights are learned for a neural network such as a deep network. Additional cognitive state data results from collecting and analyzing images of an occupant of a second vehicle. The second vehicle is manipulated based on the additional cognitive state data. The evaluating provides a cognitive state analysis. A first layer 710 of the deep network is comprised of a plurality of nodes 712. Each of the nodes 712 serves as a neuron within a neural network. The first layer can receive data from an input layer. The output of the first layer 710 feeds to the next layer 720. The layer 720 further comprises a plurality of nodes 722. A weight 714 adjusts the output of the first layer 710 which is being input to the layer 720. In embodiments, the layer 720 is a hidden layer. The output of the layer 720 feeds to a subsequent layer 730. That layer 730 further comprises a plurality of nodes 732. A weight 724 adjusts the output of the second layer 720 which is being input to the third layer 730. In embodiments, the third layer 730 is also a hidden layer. The output of the third layer 730 feeds to a fourth layer 740 which further comprises a plurality of nodes 742. A weight 734 adjusts the output of the third layer 730 which is being input to the fourth layer 740. The fourth layer 740 can be a final layer, providing a facial expression and/or cognitive state as its output. The facial expression can be identified using a hidden layer from the one or more hidden layers. The weights can be provided on inputs to the multiple layers to emphasize certain facial features within the face. The training can comprise assigning weights to inputs on one or more layers within the multi-layered analysis engine. In embodiments, one or more of the weights (714, 724, and/or 734) can be adjusted or updated during training. The assigning weights can be accomplished during a feed-forward pass through the multilayered analysis engine. In a feed-forward arrangement, the information moves forward from the input nodes through the hidden nodes and on to the output nodes. Additionally, the weights can be updated during a backpropagation process through the multilayered analysis engine.

Figure 8:
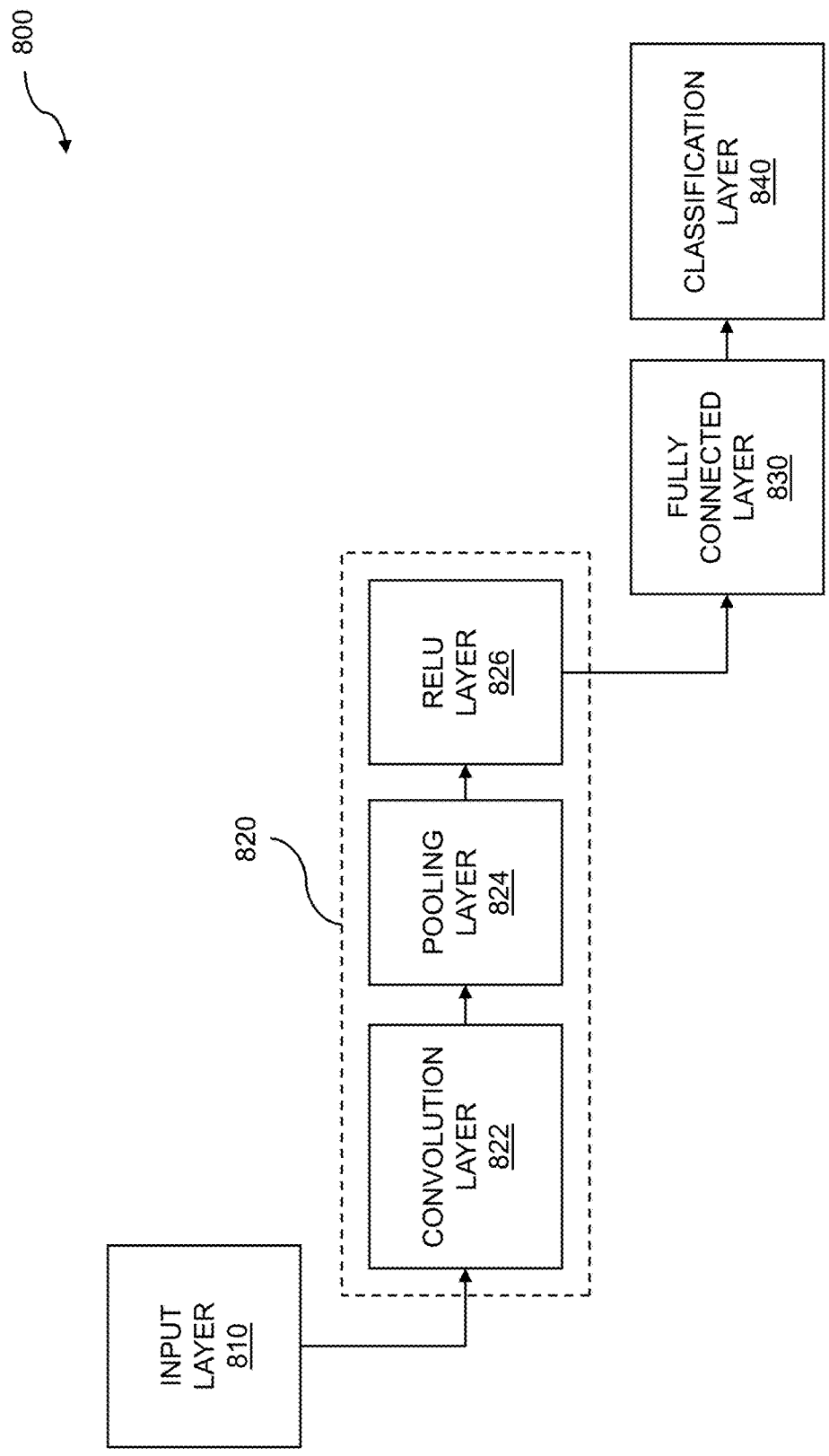
FIG. 8 is an example illustrating a convolution neural network.

FIG. 8 is an example illustrating a convolution neural network (CNN). A neural network such as this convolutional neural network 800 can be used for various applications such as deep learning. The deep learning can be applied to vehicle manipulation or navigation using cognitive state evaluation. Images of a first occupant of a first vehicle are obtained and analyzed to determine cognitive state data. Layers and weights are learned. Images of a second occupant of a second vehicle are collected and analyzed for additional cognitive state data, which is used to manipulate the second vehicle. The convolutional neural network can be applied to other tasks such as cognitive state analysis, mental state analysis, mood analysis, emotional state analysis, and so on. Cognitive state data can include mental processes, where the mental processes can include attention, creativity, memory, perception, problem solving, thinking, use of language, and the like.

Cognitive analysis is a very complex task. Understanding and evaluating moods, emotions, mental states, or cognitive states, requires a nuanced evaluation of facial expressions or other verbal and nonverbal cues that people generate. Cognitive state analysis is important in many areas such as research, psychology, business, intelligence, law enforcement, and so on. The understanding of cognitive states can be useful for a variety of business purposes such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can boost ticket sales and/or advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio data such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, volume, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 8 is an example showing a convolutional neural network 800. The convolutional neural network can be used for deep learning, where the deep learning can be applied to avatar image animation using translation vectors. The deep learning system can be accomplished using a convolution neural network or other techniques. The deep learning can perform facial recognition and analysis tasks. The network includes an input layer 810. The input layer 810 receives image data. The image data can be input in a variety of formats, such as JPEG, TIFF, BMP, and GIF. Compressed image formats can be decompressed into arrays of pixels, wherein each pixel can include an RGB tuple. The input layer 810 can then perform processing such as identifying boundaries of the face, identifying landmarks of the face, extracting features of the face, and/or rotating a face within the plurality of images.

The network includes a collection of intermediate layers 820. The multilayered analysis engine can include a convolutional neural network. Thus, the intermediate layers can include a convolution layer 822. The convolution layer 822 can include multiple sublayers, including hidden layers within it. The output of the convolution layer 822 feeds into a pooling layer 824. The pooling layer 824 performs a data reduction, which makes the overall computation more efficient. Thus, the pooling layer reduces the spatial size of the image representation to reduce the number of parameters and computations in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer as part of pooling layer 824. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 826. The output of the pooling layer 824 can be input to the RELU layer 826. In embodiments, the RELU layer implements an activation function such as $f(x)=\max(0,x)$, thus providing an activation with a threshold at zero. In some embodiments, the RELU layer 826 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can comprise multiple layers that include one or more convolutional layers 822 and one or more hidden layers, and wherein the multilayered analysis engine can be used for emotional analysis.

The example 800 includes a fully connected layer 830. The fully connected layer 830 processes each pixel/data point from the output of the collection of intermediate layers 820. The fully connected layer 830 takes all neurons in the previous layer and connects them to every single neuron it has. The output of the fully connected layer 830 provides input to a classification layer 840. The output of the classification layer 840 provides a facial expression and/or cognitive state. Thus, a multilayered analysis engine such as the one depicted in FIG. 8 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and sub-optimal actions are not explicitly corrected. Rather, on-line or computational performance is the focus. On-line performance includes finding a balance between exploration of new (uncharted) territory or spaces and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect, the person spending more time playing an online game or navigating a webpage, the person converting by buying a product or service, and so on. The reinforced learning can be based on exploring a solution space and adapting the model, algorithm, etc., based on outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 9:
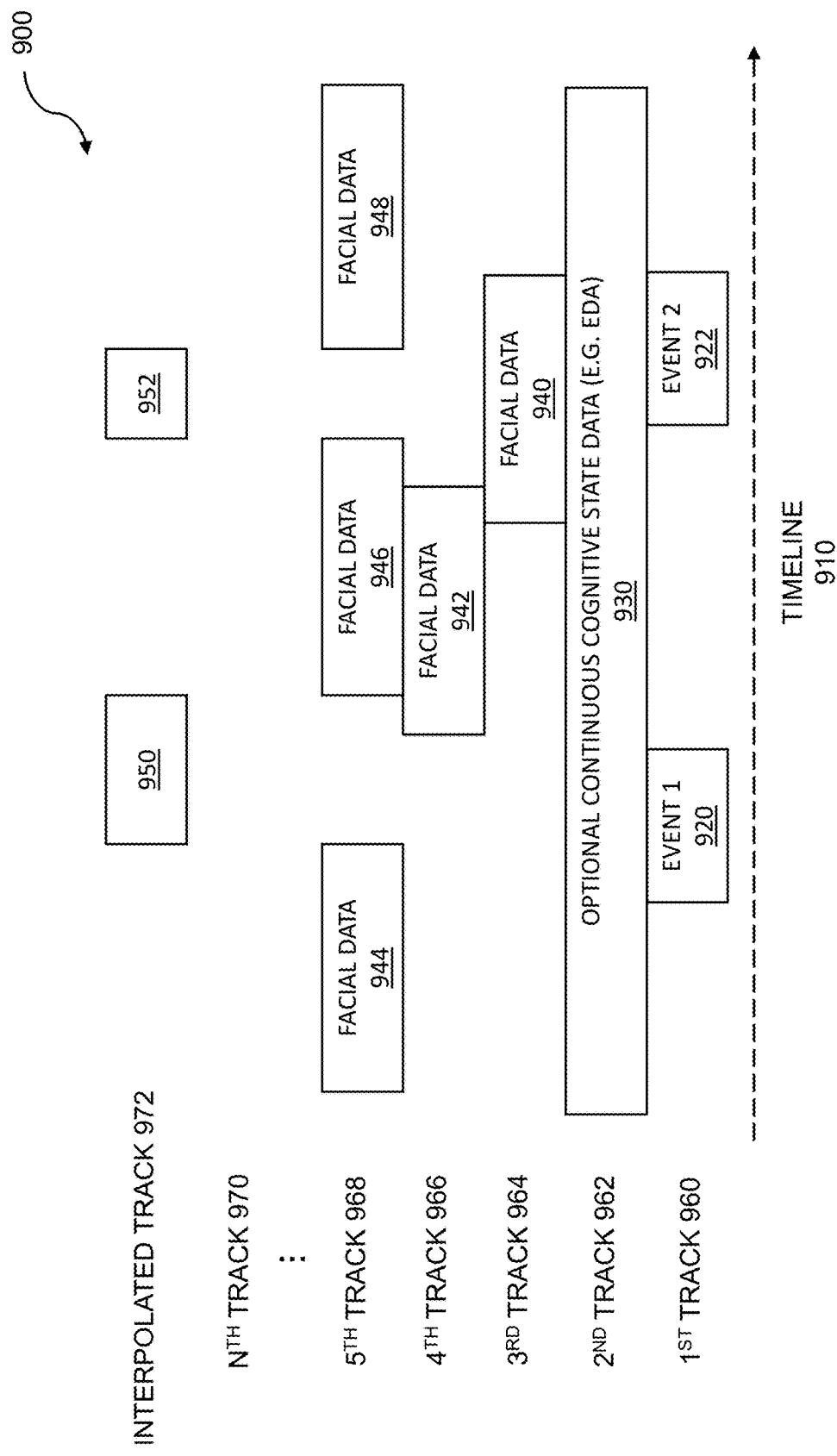
FIG. 9 is a timeline with information tracks relating to cognitive states.

FIG. 9 is a timeline with information tracks relating to cognitive states. A timeline can show one or more cognitive states that can be experienced by a vehicle occupant. The timeline can be based on vehicular cognitive data collection using multiple devices. Using an imaging device, images of a first occupant of a first vehicle are obtained and analyzed for cognitive state data. Layers and weights are learned. Images of a second occupant of a second vehicle are obtained and analyzed for additional cognitive state data. The second vehicle is manipulated using the additional cognitive state data, analyzed using the learned layers and weights. The timeline 910 with information tracks 900 relates to various cognitive states. A first track 960 shows events that, in embodiments, are related to use of a computer by the individual. A first event 920 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply to save contextual information in the first track 960. A second event 922 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 962 can include continuously collected cognitive state data 930, such as electrodermal activity data. A third track 964 can include facial data. The facial data can be collected intermittently when the individual is looking toward a camera. The facial data 940 can include one or more still photographs, videos, or abstracted facial expressions which can be collected when the user looks in the direction of the camera. A fourth track 966 can include facial data that is collected either intermittently or continuously by a second camera. The facial data 942 can include one or more still photographs, videos, or abstracted facial expressions which can be collected when the user looks in the direction of that camera. A fifth track 968 can include facial data that is collected from a third camera, such as the webcam. In the example shown, the fifth track 968 includes first facial data 944, second facial data 946, and third facial data 948, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence or the data from the multiple tracks can be combined.

Additional tracks, through the $n^{th}$ track 970, of cognitive state data of any type can be collected. The additional tracks 970 can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 972 can be included and can be associated with cognitive state data that is collected on an intermittent basis, such as the facial data of the fifth track 968. Interpolated data 950 and further interpolated data 952 can contain interpolations of the facial data of the fifth track 968 for the time periods where no facial data was collected in that track. Other embodiments interpolated data for periods where no track includes facial data. In other embodiments, analysis includes interpolating cognitive state analysis when the cognitive state data collected is intermittent.

The cognitive state data, such as the continuous cognitive state data 930 and/or any of the collected facial data 940, 942, 944, 946, and 948, can be tagged. The tags can include metadata related to the cognitive state data, including, but not limited to, the device that collected the cognitive state data; the individual from whom the cognitive state data was collected; the task being performed by the individual; the media being viewed by the individual; and the location, environcognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services. As such the tags can be used locally on the machine where the cognitive state data was collected and/or remotely on a remote server or a cloud/web service.

Other tags can be related to the cognitive state data. Further embodiments can include tagging the cognitive state data with sensor data. The sensor data can be obtained from the vehicle occupant along with the obtaining of the video data or the audio data, instead of obtaining the video data or the audio data, etc. In embodiments, the sensor data can include one or more of vehicle temperature, outside temperature, time of day, amount of daylight, weather conditions, headlight activation, windshield wiper activation, entertainment center selection, or entertainment center volume. Other sensor data can include physiological data related to one or more occupants of the vehicle. The physiological data can include heart rate, heart rate variability, electrodermal activity, acceleration, and the like. The tags can also be related to the cognitive state that can be determined by image-based analysis of the video, audio, or physiological data, or other techniques. In embodiments, the tags that can be applied can be based on one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 10:
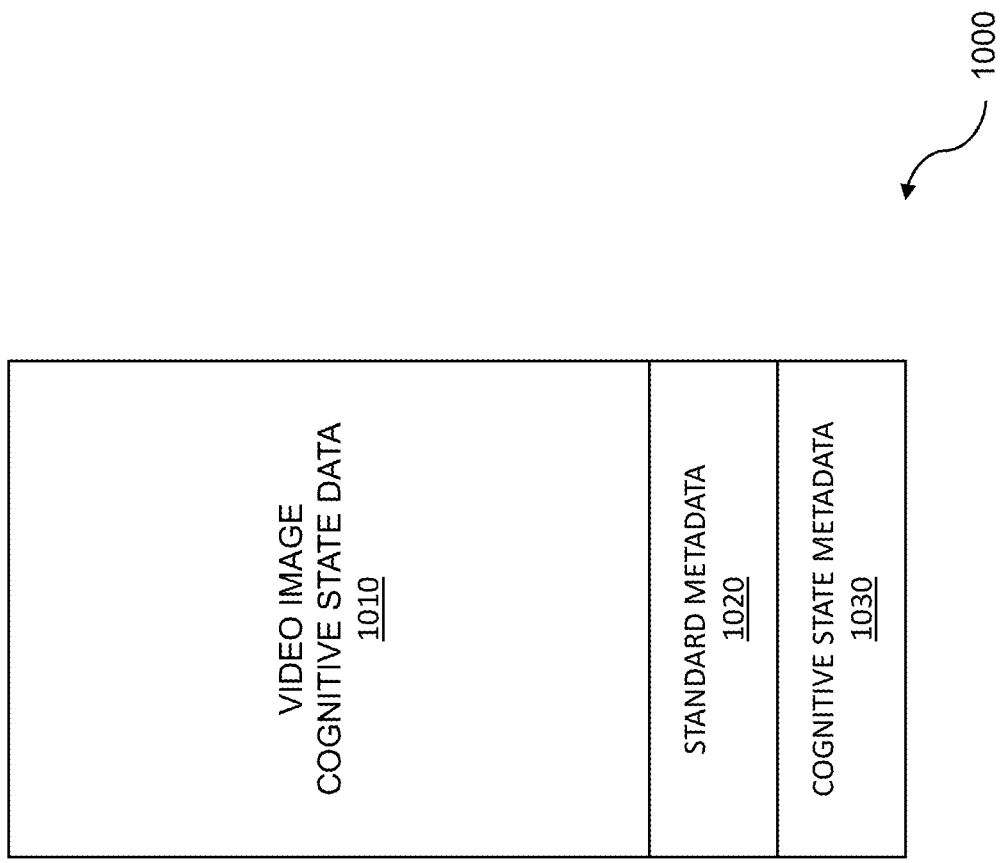
FIG. 10 shows cognitive state data with tags.

FIG. 10 shows cognitive state data with tags. Cognitive state data, including cognitive state data with tags, can be used for vehicle navigation that uses cognitive state evaluation. Images of a first occupant of a first vehicle are collected and analyzed for cognitive state data. Layers and weights of a neural network are learned. Images of a second occupant of a second vehicle are collected and analyzed for additional cognitive state data. The second vehicle is manipulated based on the additional cognitive state data. The cognitive state data, such as the cognitive state data with tags 1000, includes video image cognitive state data 1010 captured on an individual from a first source. In some embodiments, the source of the cognitive state data includes certain standard metadata 1020 with the cognitive state data 1010. For example, a video camera which includes timestamps along with video data demonstrates such metadata inclusion. A still camera which includes EXIF (or Exif) data identifying the camera model, exposure information, and day and date information in the JPEG or other image file format containing the compressed image data shows another instance of metadata inclusion.

In embodiments, additional data which provides information about the cognitive state data 1010 is determined. Such additional data can be tagged to the cognitive state data as cognitive state metadata 1030. The cognitive state metadata 1030 can provide information about the cognitive states useful in the analysis of the cognitive state data 1010. In embodiments, the cognitive state can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state metadata 1030, or additional data, is data that is not tagged to the cognitive state data by the source of the cognitive state data and not always known to the source of the cognitive state data 1010. Thus, the cognitive state metadata 1030 is tagged to the cognitive state data 1010 by an entity that is not the original source of the cognitive state data.

In one embodiment, a video camera is used to capture the cognitive state data 1010. The video camera can include standard metadata 1020 such as time and date and model number of the camera, along with the video image, which in this case comprises video image cognitive state data 1010, in a MPEG-4 data stream that is sent from the video camera to a cognitive state data collection machine. The standard metadata 1020 can be included using standard metadata formats defined by the MPEG-4 specification. The cognitive state data collection machine can determine an identity of the individual being monitored, based on a login ID, and an activity of that individual, such as watching a particular media presentation. The cognitive state data collection machine can then tag the video image with the login ID and the name of the particular media presentation as cognitive state metadata 1030. In at least one embodiment, the cognitive state data collection machine formats the cognitive state metadata as XMP metadata and includes it in the MPEG-4 file. Other embodiments determine different additional information to be used as cognitive state metadata 1030 and use different formats to tag the cognitive state data 1010 with the cognitive state metadata 1030.

Once the data collection machine has captured cognitive state data, at least a portion of the cognitive state data tagged with the additional data is sent to a web service. The portion of the cognitive state data sent to the web service can be based on the additional contextual data collected or can be based on cognitive state metadata 1030. At the web service, portions of cognitive state data can be selected for analysis based, at least in part, on tags identifying one or more contexts. In at least one embodiment, the selected portions are based, at least in part, on identifying a particular individual. In some embodiments, the selected portions include tags identifying at least two different timestamps so that samples can be distributed over a period of time. In some embodiments, the selected portions are based, at least in part, on tags identifying a particular context. Once the portions are selected, they can be analyzed by the web service and can be used to create cognitive state information.

Figure 11:
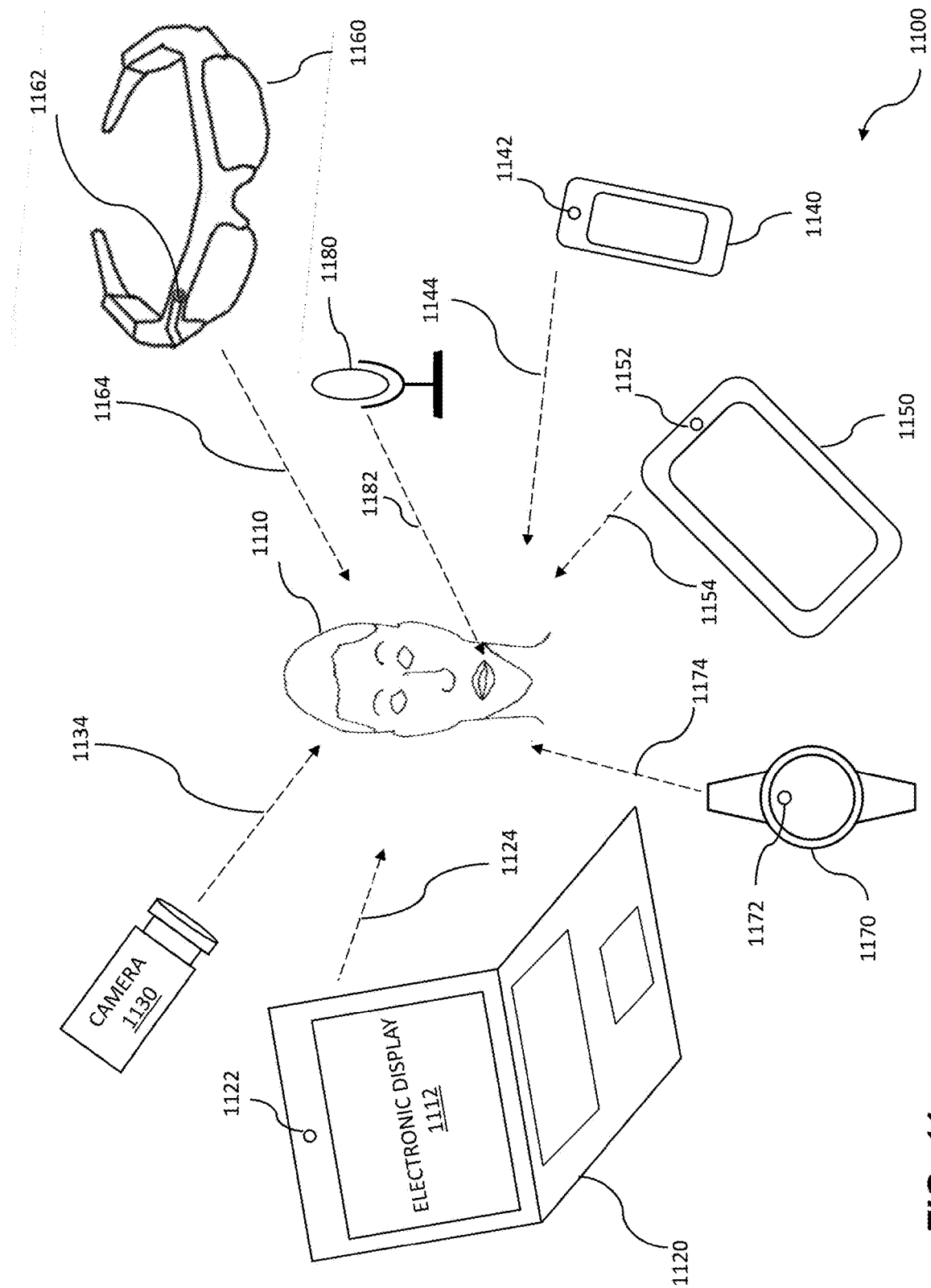
FIG. 11 shows example image and audio collection including multiple mobile devices.

FIG. 11 shows example image and audio collection including multiple mobile devices. Cognitive state data including image data, facial data, audio data, voice data, physiological data, and so on, can be collected using multiple mobile devices. The collected cognitive state data can be used for vehicle manipulation or vehicle navigation. The vehicle manipulation uses cognitive state data evaluation for vehicle navigation. Images including facial data of an occupant of a first vehicle are obtained and analyzed to determine cognitive state data. Layers and weights are learned. Images of a second occupant of a second vehicle are collected and analyzed for additional cognitive state data. The second vehicle is manipulated based on the additional cognitive state data. While one person is shown, in practice the video data or audio data on any number of people can be collected.

In the diagram 1100, the multiple mobile devices can be used separately or in any combination to collect video data, audio data, or both video and audio data on a user 1110. While one person is shown, the video data and audio data can be collected on multiple people. A user 1110 can be observed as she or he is performing a task, experiencing an event, viewing a media presentation, and so on. The user 1110 can be shown one or more media presentations, political presentations, social media, or another form of displayed media. The one or more media presentations can be shown to a plurality of people. The media presentations can be displayed on an electronic display 1112 or another display. The data collected on the user 1110 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 1110 can be analyzed and viewed for a variety of purposes including expression analysis, cognitive state analysis, mental state analysis, emotional state analysis, and so on. The electronic display 1112 can be on a laptop computer 1120 as shown, a tablet computer 1150, a cell phone 1140, a television, a mobile monitor, or any other type of electronic device. In one embodiment, video data including expression data is collected on a mobile device such as a cell phone 1140, a tablet computer 1150, a laptop computer 1120, or a watch 1170. Similarly, the audio data including speech data and non-speech vocalizations can be collected on one or more of the mobile devices. Thus, the multiple sources can include at least one mobile device, such as a phone or cell phone 1140 or a tablet 1150, or a wearable device such as a watch 1170 or glasses 1160. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 1122, a phone camera 1142, a tablet camera 1152, a wearable camera 1162, and a mobile camera 1130. A wearable camera can comprise various camera devices, such as a watch camera 1172. Sources of audio data 1182 can include a microphone 1180.

As the user 1110 is monitored, the user might move due to the nature of the task, boredom, discomfort, distractions, or for another reason. As the user moves, the camera with a view of the user's face can be changed. Thus, as an example, if the user is looking in a first direction, the line of sight 1124 from the webcam 1122 is able to observe the user's face, but if the user is looking in a second direction, the line of sight 1134 from the mobile camera 1130 is able to observe the user's face. Furthermore, in other embodiments, if the user is looking in a third direction, the line of sight 1144 from the phone camera 1142 is able to observe the user's face, and if the user is looking in a fourth direction, the line of sight 1154 from the tablet camera 1152 is able to observe the user's face. If the user is looking in a fifth direction, the line of sight 1164 from the wearable camera 1162, which can be a device such as the glasses 1160 shown and can be worn by another user or an observer, is able to observe the user's face. If the user is looking in a sixth direction, the line of sight 1174 from the wearable watch-type device 1170, with a camera 1172 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1110 can also use a wearable device including a camera for gathering contextual information and/or collecting expression data on other users. Because the user 1110 can move her or his head, the facial data can be collected intermittently when she or he is looking in a direction of a camera. In some cases, multiple people can be included in the view from one or more cameras, and some embodiments include filtering out faces of one or more other people to determine whether the user 1110 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 12:
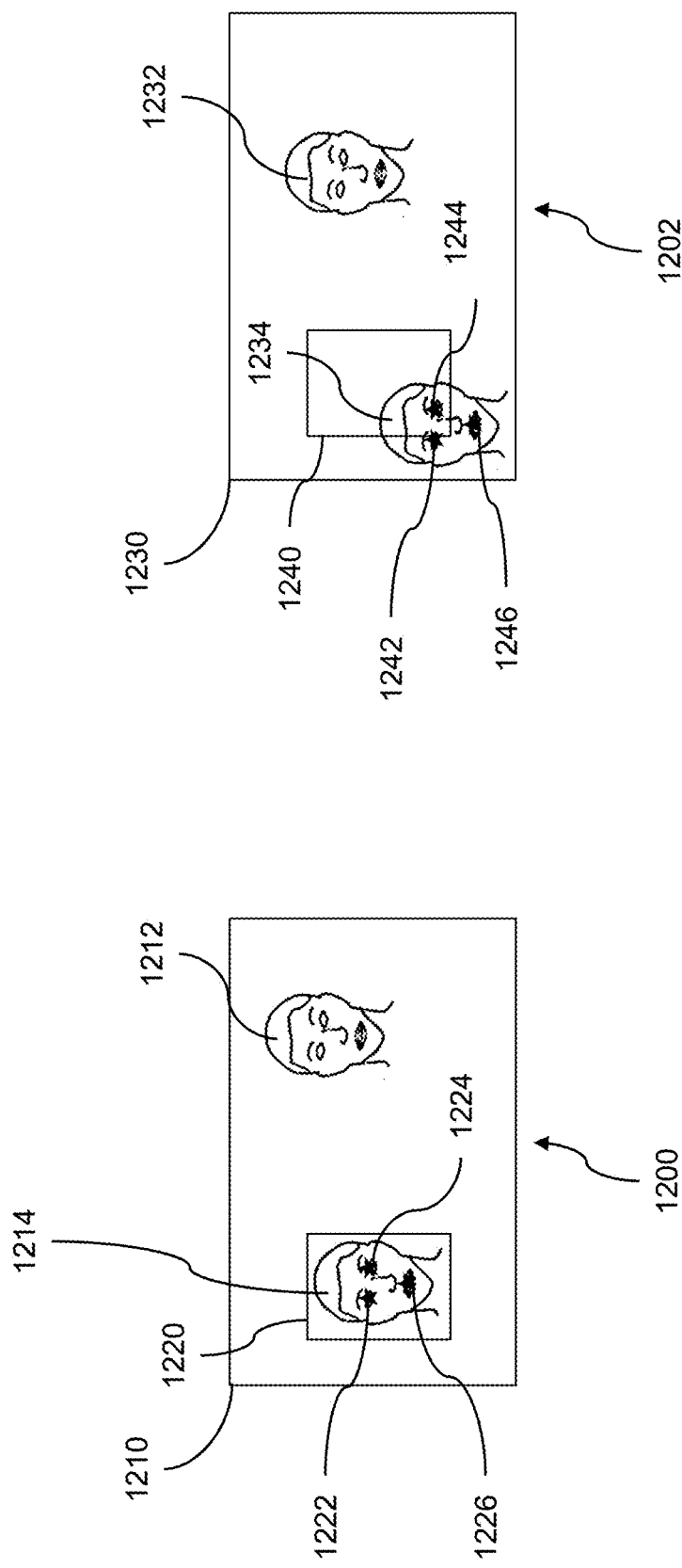
FIG. 12 illustrates feature extraction for multiple faces.

FIG. 12 illustrates feature extraction for multiple faces. Image analysis and image processing, including facial analysis and processing, can be based on feature extraction from multiple faces. Vehicle navigation uses cognitive state evaluation. Images of a first occupant of a first vehicle are obtained using a first imaging device such as a camera within the first vehicle. The one or more images include facial data of the first occupant. A first computing device is used to analyze the images to determine cognitive state data. A set of layers and weights is learned based on the cognitive state data. Images of a second occupant of a second vehicle are collected and analyzed to determine additional cognitive state data. The second vehicle is manipulated based on the additional cognitive state data that was analyzed using the set of layers and weights that were learned.

The feature extraction for multiple faces can be performed for faces that can be detected in multiple images. In embodiments, the features of multiple faces are extracted for evaluating cognitive states. Features of a face or a plurality of faces can be extracted from collected video data. The feature extraction can be performed by analysis, by using one or more processors, by using one or more video collection devices, and by using a server. The analysis device can be used to perform face detection for a second face, as well as to perform facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; of detecting the one or more faces in one or more videos; of detecting facial features and landmarks; and so on. The observations can be analyzed based on one or more of a set of quantifiable properties. The properties can be described as features and explanatory variables involving various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, etc. Algorithms for classification can be implemented using a variety of techniques, including neural networks, kernel estimation, support vector machines, use of quadratic surfaces, and so on. Classification can be used in many application areas such as computer vision and speech and handwriting recognition. Classification can be used for biometric identification of one or more people in a single frame or in multiple frames of one or more videos.

Returning to FIG. 12, the detection of the first face, the second face, and multiple faces can include identifying facial landmarks, generating a bounding box, and predicting a bounding box and landmarks for a next frame, where the next frame can be one of a plurality of frames of a video containing faces. A first video frame 1200 includes a frame boundary 1210, a first face 1212, and a second face 1214. The video frame 1200 also includes a bounding box 1220. Facial landmarks can be generated for the first face 1212. Face detection can be performed to initialize a second set of locations for a second set of facial landmarks for a second face within the video. Facial landmarks in the video frame 1200 can include the facial landmarks 1222, 1224, and 1226. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. The estimating of a second rough bounding box can include the bounding box 1220. Bounding boxes can also be estimated for one or more other faces within the boundary 1210. The bounding box can be refined, as can one or more facial landmarks. The refining of the second set of locations for the second set of facial landmarks can be based on localized information around the second set of facial landmarks. The bounding box 1220 and the facial landmarks 1222, 1224, and 1226 can be used to estimate future locations for the second set of locations for the second set of facial landmarks in a future video frame from the first video frame.

A second video frame 1202 is also shown. The second video frame 1202 includes a frame boundary 1230, a first face 1232, and a second face 1234. The second video frame 1202 also includes a bounding box 1240 and the facial landmarks, or points, 1242, 1244, and 1246. In other embodiments, multiple facial landmarks are generated and used for facial tracking of the two or more faces of a video frame, such as the shown second video frame 1202. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 1240 can be estimated, where the estimating can be based on the location of the generated bounding box 1220 shown in the first video frame 1200. The three facial points shown, facial points, or landmarks, 1242, 1244, and 1246, might lie within the bounding box 1240 or might not lie partially or completely within the bounding box 1240. For instance, the second face 1234 might have moved between the first video frame 1200 and the second video frame 1202. Based on the accuracy of the estimating of the bounding box 1240, a new estimation can be determined for a third, future frame from the video, and so on. The evaluation can be performed, all or in part, using semiconductor-based logic.

Figure 13:
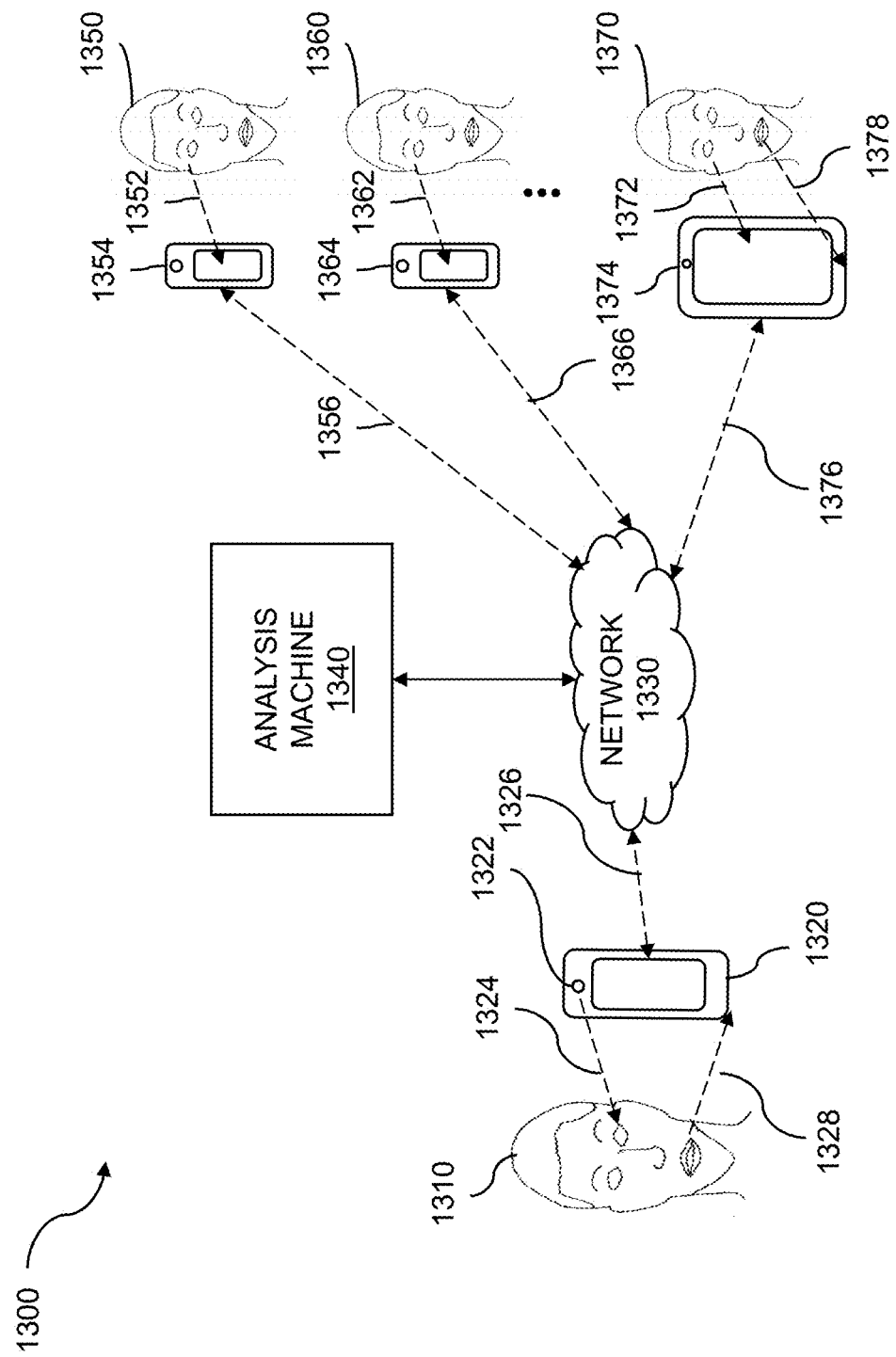
FIG. 13 shows an example of live streaming of social video and audio.

FIG. 13 shows an example of live streaming of social video and audio. The streaming of social video and social audio can be applied to vehicle navigation using cognitive state evaluation. The live streaming can include cognitive state data, image data, facial data, speech data, audio data, physiological data, etc. The cognitive state data can be determined by evaluating images of an occupant of a vehicle. The evaluating can be based on obtaining images of an occupant of a first vehicle and analyzing the images for cognitive state data. A set of layers and weights for a neural network can be learned. Additional cognitive state data can be determined by obtaining additional images of an occupant of a second vehicle and analyzing the images. The second vehicle can be manipulated based on the additional cognitive state data.

The live streaming and image analysis can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 1300 shows a user 1310 broadcasting a video live stream and an audio live stream to one or more people as shown by a first person 1350, a second person 1360, and a third person 1370. A portable, network-enabled, electronic device 1320 can be coupled to a front-side camera 1322. The portable electronic device 1320 can be a smartphone, a PDA, a tablet, a laptop computer, and so on. The front-side camera 1322 coupled to the device 1320 can have a line-of-sight view 1324 to the user 1310 and can capture video of the user 1310. The portable electronic device 1320 can be coupled to a microphone (not shown). The microphone can capture voice data 1328 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 1340 using a network link 1326 to the Internet 1330. The network link can be a wireless link, a wired link, and so on. The recommendation engine 1340 can recommend to the user 1310 an app and/or platform that can be supported by the server and can be used to provide a video live stream, an audio live stream, or both a video live stream and an audio live stream to one or more followers of the user 1310.

In the example 1300, the user 1310 has three followers: a first person 1350, a second person 1360, and a third person 1370. Each follower has a line-of-sight view to a video screen on a portable, networked electronic device. In other embodiments, one or more followers follow the user 1310 using any other networked electronic device, including a computer. In the example 1300, a first person 1350 has a line-of-sight view 1352 to the video screen of a device 1354; a second person 1360 has a line-of-sight view 1362 to the video screen of a device 1364, and a third person 1370 has a line-of-sight view 1372 to the video screen of a device 1374. The device 1374 can also capture audio data 1378 from the third person 1370. The portable electronic devices 1354, 1364, and 1374 can each be a smartphone, a PDA, a tablet, and so on. Each portable device can receive the video stream and the audio stream being broadcast by the user 1310 through the Internet 1330 using the app and/or platform that can be recommended by the recommendation engine 1340. The device 1354 can receive a video stream and the audio stream using the network link 1356, the device 1364 can receive a video stream and the audio stream using the network link 1366, the device 1374 can receive a video stream and the audio stream using the network link 1376, and so on. The network link can be a wireless link, a wired link, a hybrid link, and so on. Depending on the app and/or platform that can be recommended by the recommendation engine 1340, one or more followers, such as the followers shown 1350, 1360, and 1370, can reply to, comment on, or otherwise provide feedback to the user 1310 using their respective devices 1354, 1364, and 1374.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive affect valence provides evidence that a viewer is experiencing a favorable emotional response to the video media presentation, while negative affect valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line which runs through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 14:
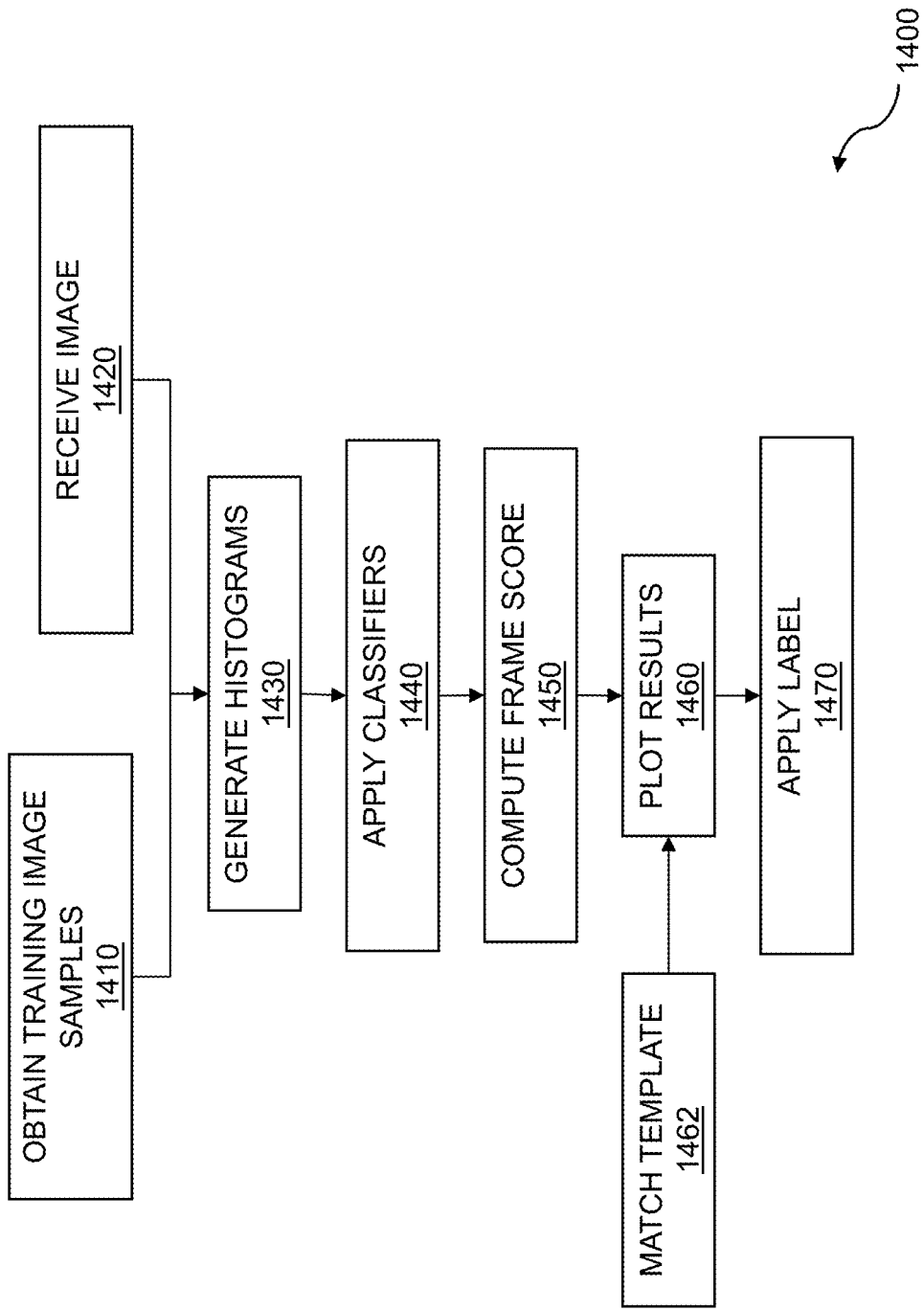
FIG. 14 is a flow diagram for detecting facial expressions.

FIG. 14 is a flow diagram for detecting facial expressions. Cognitive states can be determined by detecting and analyzing facial expressions in images. The cognitive states can be used for vehicle navigation, where the vehicle navigation can use cognitive state evaluation. Images of an occupant of a first vehicle are obtained and analyzed for cognitive state data. Layers and weights of a neural network such as a deep neural network are learned. Images of a person in a second vehicle are collected and analyzed for additional cognitive state data. The second vehicle is manipulated based on the additional cognitive state data.

The flow 1400, or portions thereof, can be implemented in semiconductor logic, can be accomplished using a mobile device, can be accomplished using a server device, and so on. The flow 1400 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller and can be used to infer a smirk.

The flow 1400 begins by obtaining training image samples 1410. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1400 continues with receiving an image 1420. The image 1420 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1400 continues with generating histograms 1430 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1400 continues with applying classifiers 1440 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1400 continues with computing a frame score 1450. The score computed for an image, where the image can be a frame from a video, can be used to determine the presence of a facial expression in the image or video frame. The score can be based on one or more versions of the image 1420 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier can be used to identify symmetrical facial expressions (e.g. smile), asymmetrical facial expressions (e.g. outer brow raiser), and so on.

The flow 1400 continues with plotting results 1460. The results that are plotted can include one or more scores for one or more frames computed over a given time t. For example, the plotted results can include classifier probability results from analysis of HoGs for a sequence of images and video frames. The plotted results can be matched with a template 1462. The template can be temporal and can be represented by a centered box function or another function. A best fit with one or more templates can be found by computing a minimum error. Other best-fit techniques can include polynomial curve fitting, geometric curve fitting, and so on. The flow 1400 continues with applying a label 1470. The label can be used to indicate that a particular facial expression has been detected in the one or more images or video frames which constitute the image 1420 that was received. The label can be used to indicate that any of a range of facial expressions has been detected, including a smile, an asymmetric smile, a frown, and so on. Various steps in the flow 1400 may be changed in order, repeated, omitted, or the like without departing from the disclosed concepts. Various embodiments of the flow 1400 can be included in a computer program product embodied in a non-transitory computer readable medium that includes code executable by one or more processors. Various embodiments of the flow 1400, or portions thereof, can be included on a semiconductor chip and implemented in special purpose logic, programmable logic, and so on.

Figure 15:
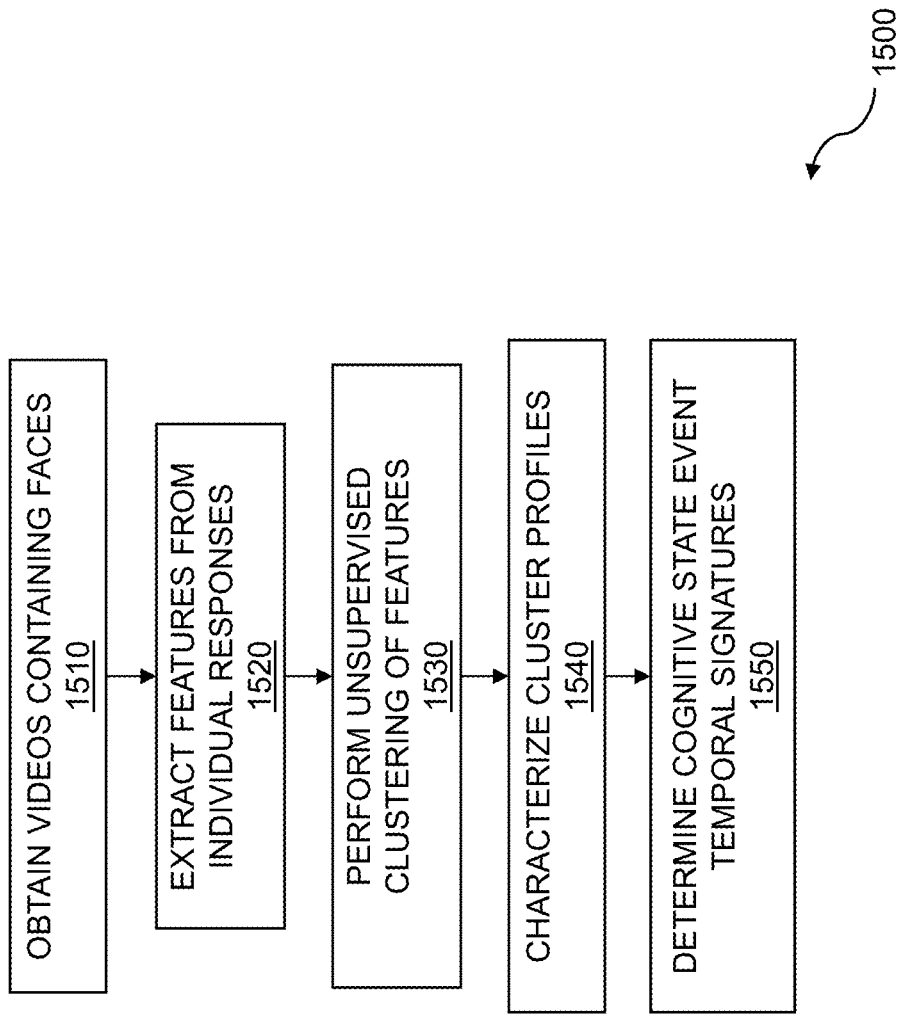
FIG. 15 is a flow diagram for the large-scale clustering of facial events.

FIG. 15 is a flow diagram for the large-scale clustering of facial events. Vehicle navigation can use cognitive state evaluation, where the evaluation can use results from large-scale clustering. Images including facial data of a vehicle occupant are obtained and analyzed to determine cognitive state data. Layers and weights of a deep neural network are learned. Images of an occupant of a second vehicle are collected and analyzed for additional cognitive state data. The second vehicle is manipulated based on the analysis of the additional cognitive state data. Cognitive state events can include facial events, speech events, etc. The large-scale clustering of facial events can be performed for data collected from a remote computing device. The facial events can be collected from people as they interact with a vehicle. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can collect data from the one or more people and can be used to render and display data to one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1500 includes obtaining videos containing faces 1510. The videos can be obtained using one or more cameras, where the cameras can include a webcam coupled to one or more devices employed by the one or more people using the web-based framework. The flow 1500 continues with extracting features from the individual responses 1520. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1500 continues with performing unsupervised clustering of features 1530. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1500 includes characterizing cluster profiles 1540. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1500 can include determining cognitive state event temporal signatures 1550. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1500 may be changed in order, repeated, omitted, or the like without departing from the disclosed concepts. Various embodiments of the flow 1500 can be included in a computer program product embodied in a non-transitory computer readable medium that includes code executable by one or more processors. Various embodiments of the flow 1500, or portions thereof, can be included on a semiconductor chip and implemented in special purpose logic, programmable logic, and so on.

Figure 16:
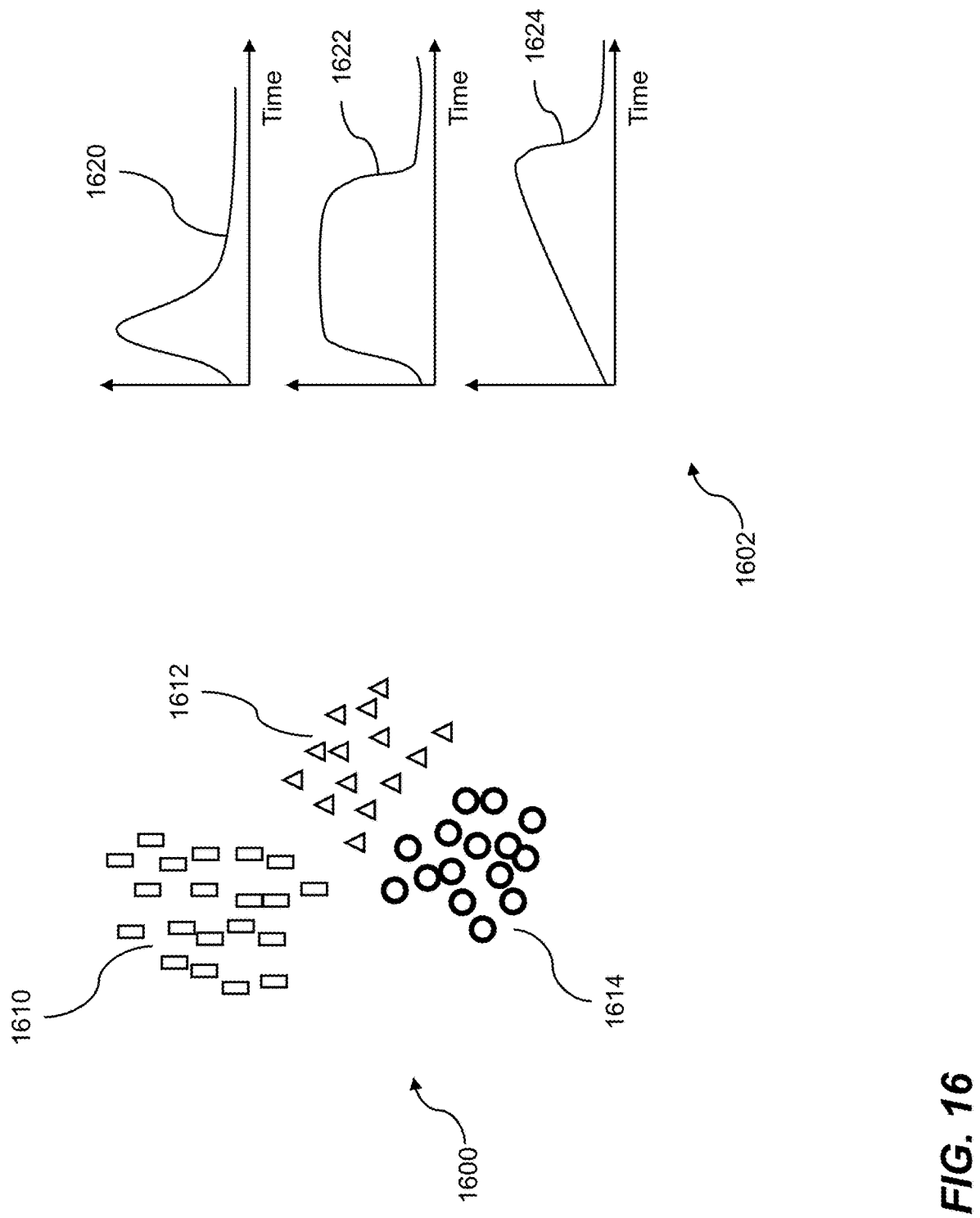
FIG. 16 shows unsupervised clustering of features and characterizations of cluster profiles.

FIG. 16 shows unsupervised clustering of features and characterizations of cluster profiles. The features can be based on image data, audio data, physiological data, and so on, collected from an occupant of a vehicle. Cognitive state evaluation can be used for vehicle navigation. Images, including facial data, are obtained and analyzed to determine cognitive state data of a vehicle occupant. Layers and weights are learned for a deep neural network. Images are collected of a second occupant of a second vehicle. The latter images are analyzed to determine additional cognitive state data. The second vehicle is manipulated based on the additional cognitive state data.

The clustering of features and characterizations of cluster profiles can be performed for data collected from a remote computing device. The clustering of features and characterizations of cluster profiles can be performed for people as they interact with a vehicle. The sub-sectional components can be used with performing the evaluation of content of the face. The sub-sectional components can be used to provide a context. Features including samples of facial data can be clustered using unsupervised clustering. Various clusters can be formed which include similar groupings of facial data observations. The example 1600 shows three clusters, clusters 1610, 1612, and 1614. The clusters can be based on video collected from people who have opted-in to video collection. When the data collected is captured using a web-based framework, the data collection can be performed on a grand scale, including hundreds, thousands, or even more participants who can be located in close proximity and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1602 can be generated based on the clusters that can be formed from unsupervised clustering, with time shown on the x-axis and intensity or frequency shown on the y-axis. The cluster profiles can be based on captured facial data, including facial expressions. The cluster profile 1620 can be based on the cluster 1610, the cluster profile 1622 can be based on the cluster 1612, and the cluster profile 1624 can be based on the cluster 1614. The cluster profiles 1620, 1622, and 1624 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 17A:
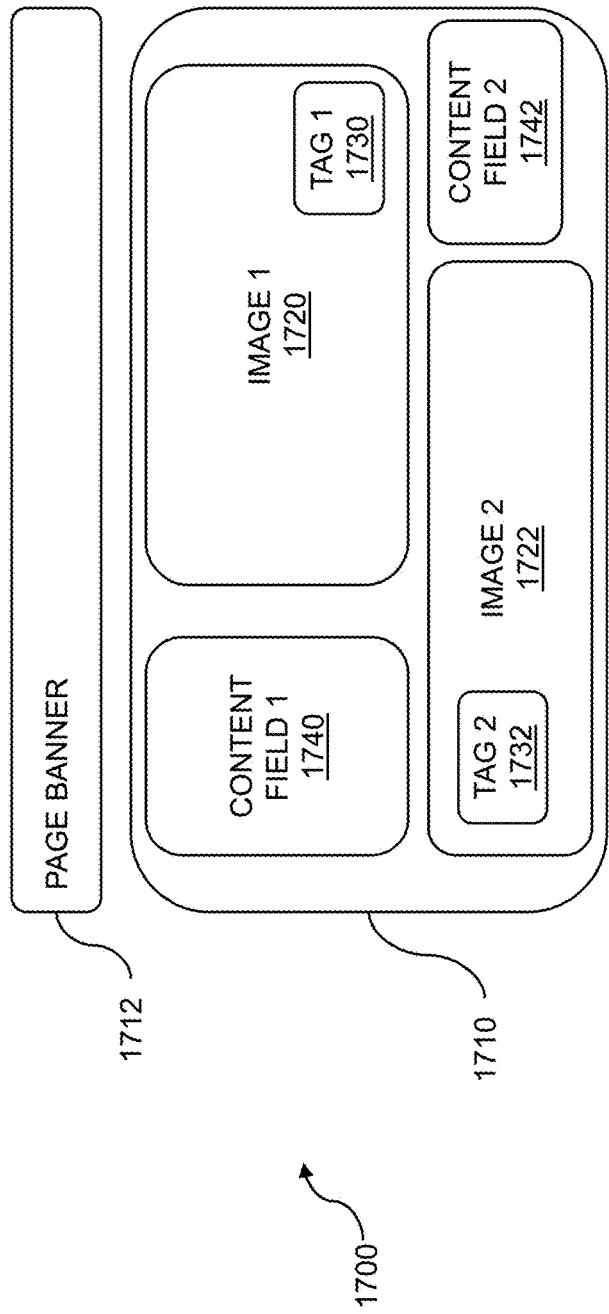
FIG. 17A shows example tags embedded in a webpage.

FIG. 17A shows example tags embedded in a webpage. Vehicle navigation uses convolutional state evaluation. In some embodiments, screens within a vehicle can use embedded tags. Images including facial data are obtained of a first occupant in a first vehicle. The images are analyzed to determine cognitive state data for the first occupant. A set of layers and weights is learned for a deep neural network. More images are collected of a second occupant of a second vehicle, and the additional images are analyzed to determine additional cognitive state data. The second vehicle is manipulated based on the additional cognitive state data. The additional cognitive state data can be analyzed by the deep neural network using the layers and weights. The tags embedded in the webpage can be used for image analysis and processing for data collected from a remote computing device. The tags embedded in the webpage can be used by people as they interact with a vehicle. Once a tag is detected, a mobile device, a server, semiconductor-based logic, etc. can be used to evaluate associated facial expressions. A webpage 1700 can include a page body 1710, a page banner 1712, and so on. The page body can include one or more objects, where the objects can include text, images, videos, audio, and so on. The example page body 1710 shown includes a first image, image 1 1720; a second image, image 2 1722; a first content field, content field 1 1740; and a second content field, content field 2 1742. In practice, the page body 1710 can contain multiple images and content fields and can include one or more videos, one or more audio presentations, and so on. The page body can include embedded tags, such as tag 1 1730 and tag 2 1732. In the example shown, tag 1 1730 is embedded in image 1 1720, and tag 2 1732 is embedded in image 2 1722. In embodiments, multiple tags are embedded. Tags can also be embedded in content fields, in videos, in audio presentations, etc. When a user mouses over a tag or clicks on an object associated with a tag, the tag can be invoked. For example, when the user mouses over tag 1 1730, tag 1 1730 can then be invoked. Invoking tag 1 1730 can include enabling a camera coupled to a user's device and capturing one or more images of the user as the user views a media presentation (or digital experience). In a similar manner, when the user mouses over tag 2 1732, tag 2 1732 can be invoked. Invoking tag 2 1732 can also include enabling the camera and capturing images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 17B:
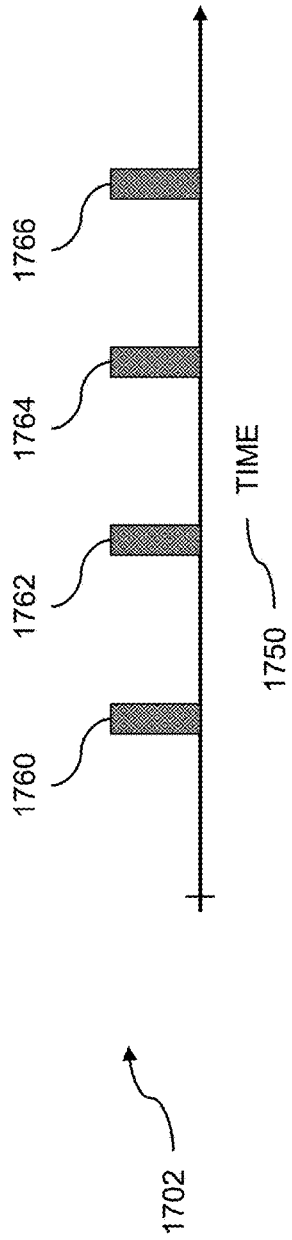
FIG. 17B shows invoking tags to collect images.

FIG. 17B shows invoking tags to collect images. Vehicle manipulation, navigation, etc., can be based on using convolutional image processing. The image processing is based on learning weights and layers for a deep neural network. The weights and layers are learned by analyzing images, including facial data, obtained of a vehicle occupant. The deep neural network is used to analyze further images of persons in a second vehicle. The second vehicle is manipulated based on the additional cognitive state data that was analyzed using the weights and layers. The invoking tags to collect images can be used in image analysis for data collected from a remote computing device. The invoking tags to collect images can be used for people as they interact with a vehicle. As previously stated, a media presentation can be a video, a webpage, and so on. A video 1702 can include one or more embedded tags, such as a tag 1760, a second tag 1762, a third tag 1764, a fourth tag 1766, and so on. In practice, multiple tags can be included in the media presentation. The one or more tags can be invoked during the media presentation. The collection of the invoked tags can occur over time, as represented by a timeline 1750. When a tag is encountered in the media presentation, the tag can be invoked. When the tag 1760 is encountered, invoking the tag can enable a camera coupled to a user device and can capture one or more images of the user viewing the media presentation. Invoking a tag can depend on an opt-in selection made by the user. For example, if a user has agreed to participate in a study by indicating an opt-in, then the camera coupled to the user's device can be enabled and one or more images of the user can be captured. If the user has not agreed to participate in the study and has indicated an opt-out, then invoking the tag 1760 neither enables the camera nor captures images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages, advertising messages, social media sharing, etc. and that enable the camera and image capture when invoked would be embedded in the corresponding media presentation. However, tags embedded in the media presentation that are related to advertisements would not enable the camera when invoked. Various other situations of tag invocation are also possible.

Figure 18:
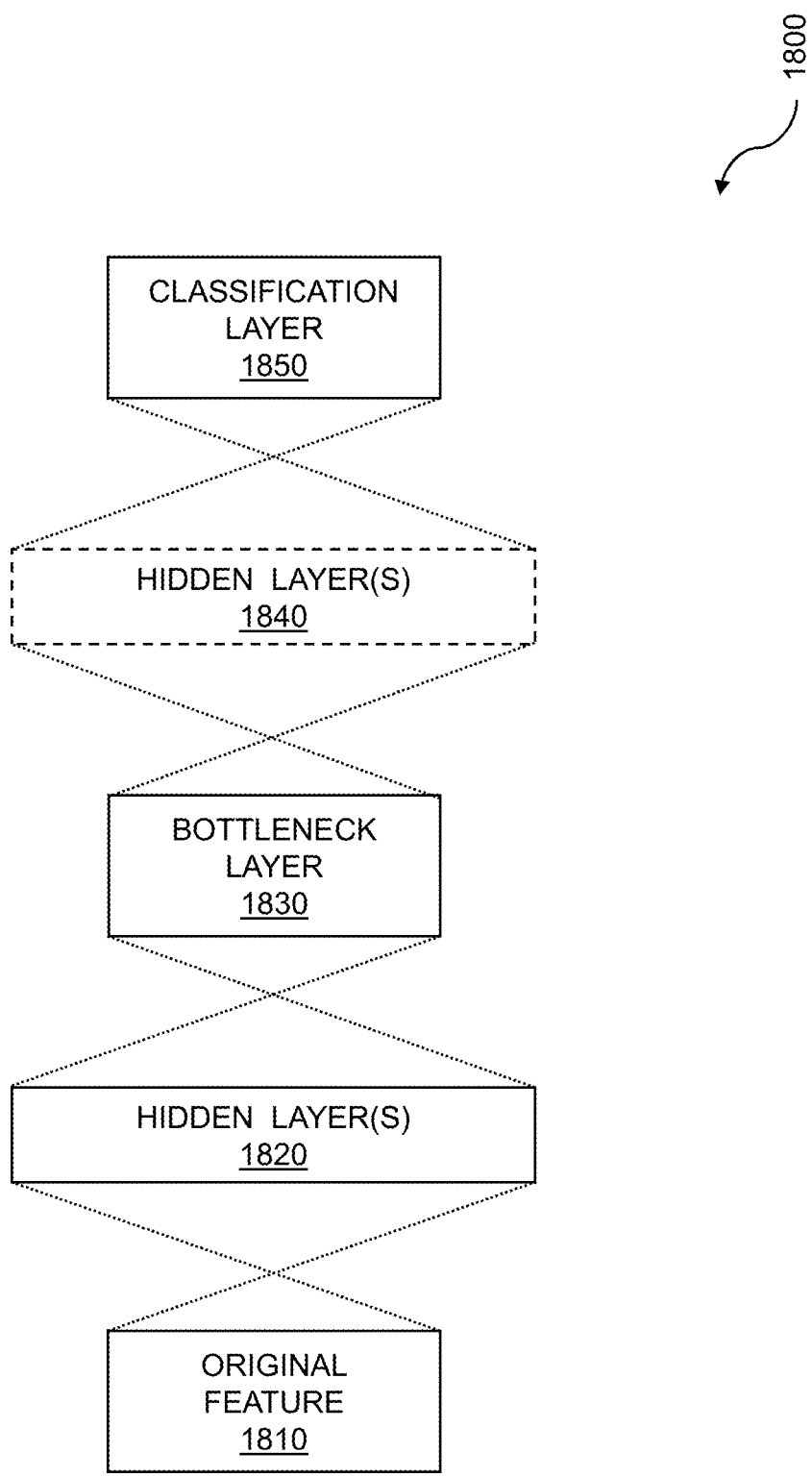
FIG. 18 illustrates a bottleneck layer within a deep learning environment.

FIG. 18 illustrates a bottleneck layer within a deep learning environment. A plurality of layers in a deep neural network (DNN) can include a bottleneck layer. The bottleneck layer can be used for vehicle manipulation, where the vehicle manipulation can include cognitive state evaluation for vehicle navigation. A deep neural network can include layers and can apply weights learned by analyzing cognitive state data. Images including facial data are obtained using an imaging device. The images are analyzed to determine cognitive state data. Layers and weights for a neural network are learned. Further images are collected of one or more people in a second vehicle, and the images are analyzed to determine additional cognitive state data. The second vehicle is manipulated based on analysis by the deep neural network of the additional cognitive state data.

Layers of a deep neural network can include a bottleneck layer 1800. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1810. A feature such as an image feature can include points, edges, objects, boundaries between and among regions, properties, and so on. The deep neural network can include one or more hidden layers 1820. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1830. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1840. The number of the hidden layers can include zero hidden layers, one hidden layer, a plurality of hidden layers, and so on. The hidden layers following the bottleneck layer can include more nodes than the bottleneck layer. The deep neural network can include a classification layer 1850. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 19:
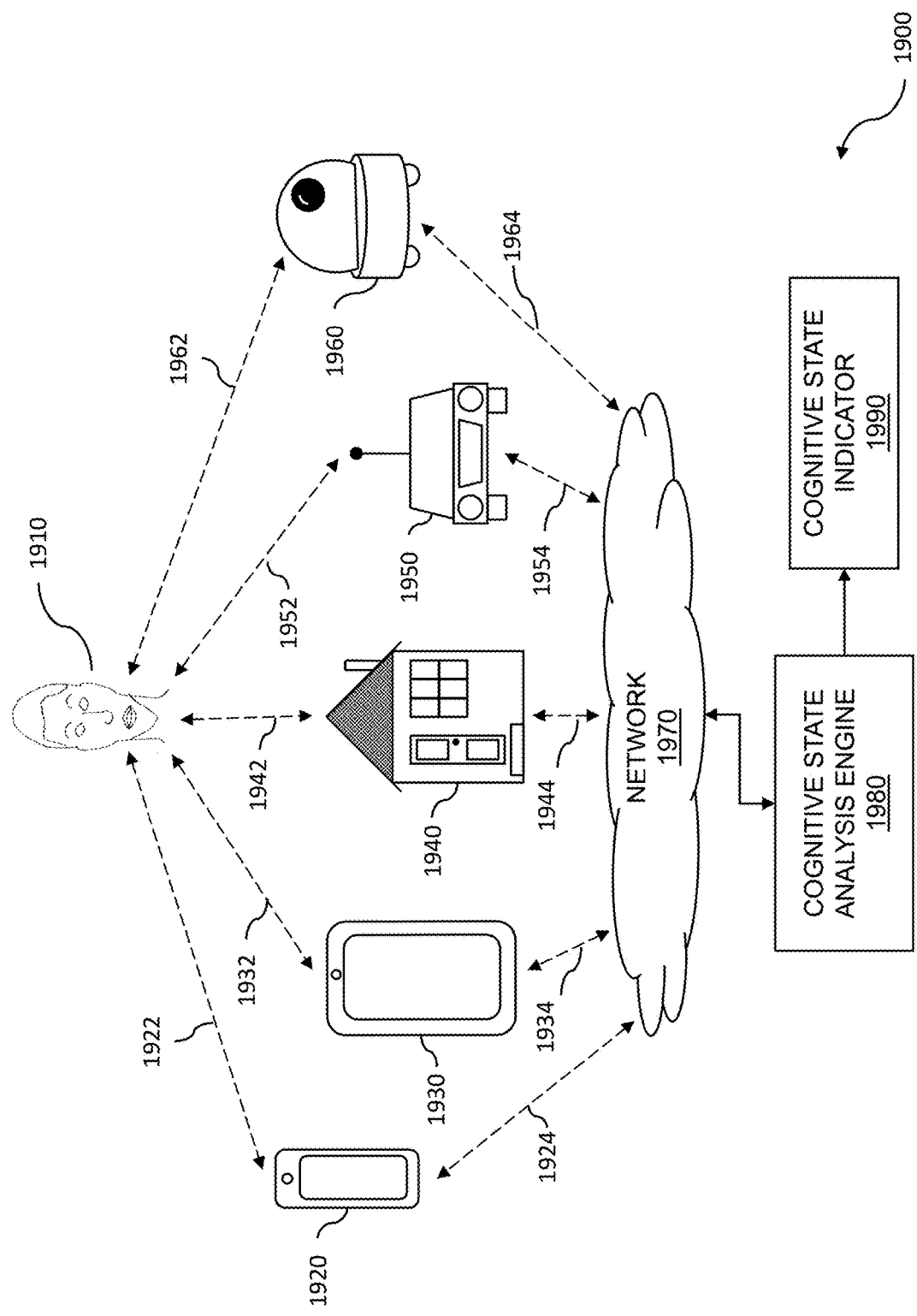
FIG. 19 shows data collection including multiple devices and locations.

FIG. 19 shows data collection including multiple devices and locations 1900. Video data, audio data, or physiological data can be obtained and analyzed for cognitive state data. The cognitive state data is used for cognitive state evaluation for vehicle navigation. The cognitive state can be based on learning layers and weights for a neural network. The layers and weights can be used for vehicle manipulation, navigation, and so on. The data can be obtained for one or more individuals from multiple devices, vehicles, and locations. The images and facial data can be obtained from an imaging device that can be located within a vehicle or building, coupled to an electronic device, and so on. Images or other data can be collected for an occupant of a second vehicle. The images can be analyzed to determine additional cognitive state data. The second vehicle can be manipulated based on the additional cognitive state data.

The multiple mobile devices, vehicles, and locations 1900 can be used separately or in combination to collect video data on a user 1910. The video data can include facial data, image data, etc. Other data such as audio data, physiological data, and so on, can be collected on the user. While one person is shown, the video data, or other data, can be collected on multiple people. A user 1910 can be observed as she or he is performing a task, experiencing an event, viewing a media presentation, and so on. The user 1910 can be shown one or more media presentations, political presentations, social media, or another form of displayed media. The one or more media presentations can be shown to a plurality of people. The media presentations can be displayed on an electronic display coupled to a client device. The data collected on the user 1910 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1910 can be analyzed and viewed for a variety of purposes including expression analysis, mental state analysis, cognitive state analysis, and so on. The electronic display can be on a smartphone 1920 as shown, a tablet computer 1930, a personal digital assistant, a television, a mobile monitor, or any other type of electronic device. In one embodiment, expression data is collected on a mobile device such as a cell phone 1920, a tablet computer 1930, a laptop computer, or a watch. Thus, the multiple sources can include at least one mobile device, such as a phone 1920 or a tablet 1930, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1910, data can be collected in a house 1940 using a web camera or the like; in a vehicle 1950 using a web camera, client device, etc.; by a social robot 1960, and so on.

As the user 1910 is monitored, the user 1910 might move due to the nature of the task, boredom, discomfort, distractions, or for another reason. As the user moves, the camera with a view of the user's face can be changed. Thus, as an example, if the user 1910 is looking in a first direction, the line of sight 1922 from the smartphone 1920 is able to observe the user's face, but if the user is looking in a second direction, the line of sight 1932 from the tablet 1930 is able to observe the user's face. Furthermore, in other embodiments, if the user is looking in a third direction, the line of sight 1942 from a camera in the house 1940 is able to observe the user's face, and if the user is looking in a fourth direction, the line of sight 1952 from the camera in the vehicle 1950 is able to observe the user's face. If the user is looking in a fifth direction, the line of sight 1962 from the social robot 1960 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1910 can also use a wearable device including a camera for gathering contextual information and/or collecting expression data on other users. Because the user 1910 can move her or his head, the facial data can be collected intermittently when she or he is looking in a direction of a camera. In some cases, multiple people can be included in the view from one or more cameras, and some embodiments include filtering out faces of one or more other people to determine whether the user 1910 is looking toward a camera. All or some of the expression data can be continuously or sporadically available from the various devices and other devices.

The captured video data can include cognitive content, such as facial expressions, etc., and can be transferred over a network 1970. The network can include the Internet or other computer network. The smartphone 1920 can share video using a link 1924, the tablet 1930 using a link 1934, the house 1940 using a link 1944, the vehicle 1950 using a link 1954, and the social robot 1960 using a link 1964. The links 1924, 1934, 1944, 1954, and 1964 can be wired, wireless, and hybrid links. The captured video data, including facial expressions, can be analyzed on a cognitive state analysis engine 1980, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1990. The cognitive state indicator 1990 can indicate cognitive states, mental states, moods, emotions, etc. Further embodiments include inferring a cognitive state based on emotional content within a face detected within the facial image data, wherein the cognitive state includes of one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 20:
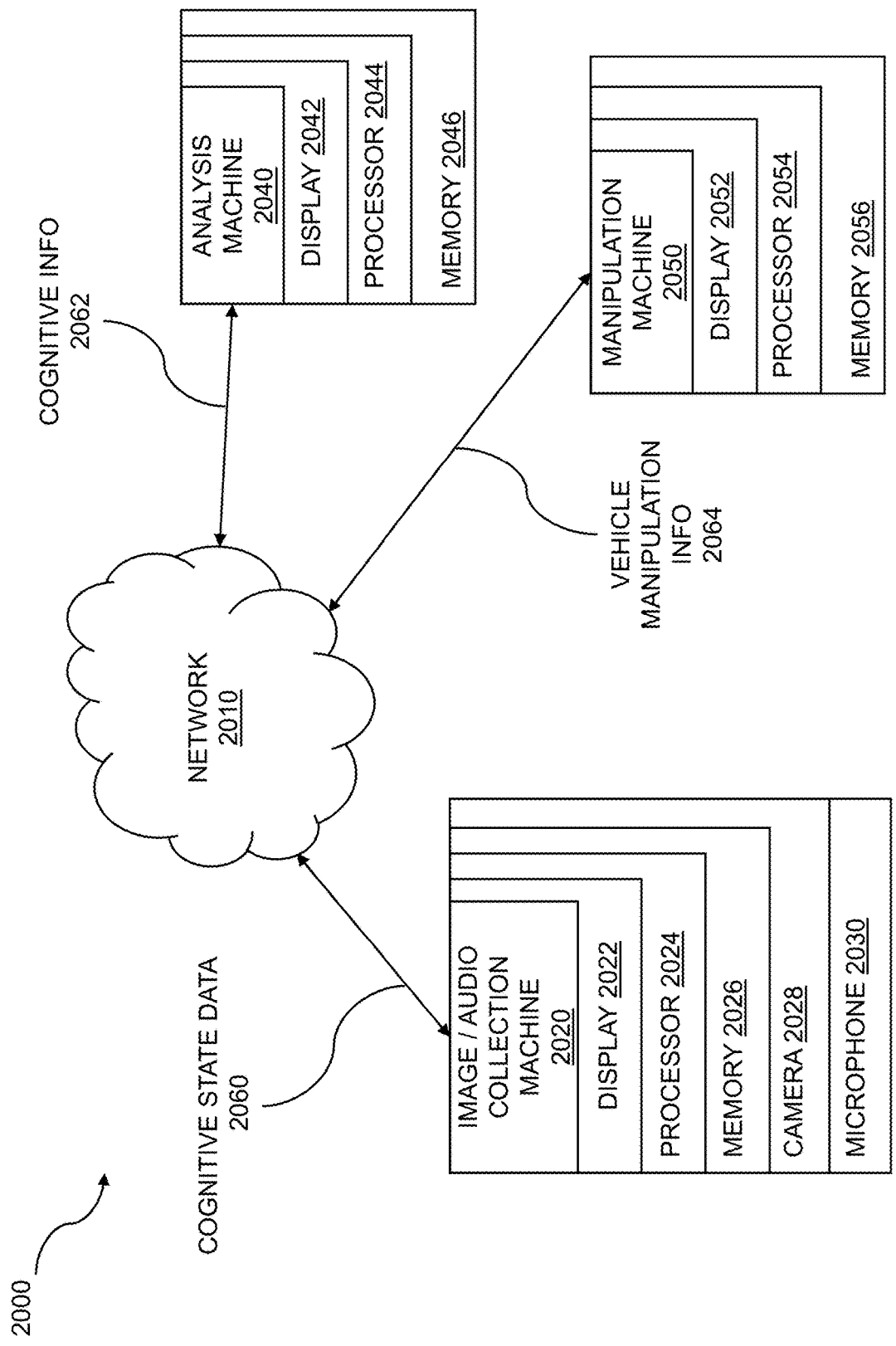
FIG. 20 is a diagram of a system for system diagram for vehicle manipulation.

FIG. 20 is a diagram of a system 2000 for vehicle manipulation. Vehicle manipulation including vehicle navigation is based on cognitive state evaluation. One or more images of a first occupant of a first vehicle are obtained using a first imaging device. The first imaging device such as a camera can be located within the first vehicle. The one or more images include facial data of the first occupant. A first computing device is used to analyze the one or more images to determine cognitive state data for the first occupant. The cognitive state data can be augmented based on audio data collected on the first occupant. The audio information can include speech or non-speech vocalizations. The non-speech vocalizations can include grunts, yelps, squeals, snoring, sighs, laughter, filled pauses, unfilled pauses, or yawns. A set of layers and weights is learned based on the cognitive state data. The learning can be performed based on a neural network such as deep neural network, a convolutional neural network, a recursive neural network, and so on. One or more images are collected of a second occupant of a second vehicle. The one or more images of the second occupant are analyzed to determine additional cognitive state data. The additional cognitive state data can be augmented. The additional cognitive state data can be augmented based on audio data collected on the second occupant. The additional cognitive state data can be based on physiological data collected on the second occupant. The physiological data can include skin conductance or galvanic skin response, heartrate, heartrate variability, or respiratory rate. The second vehicle is manipulated based on the additional cognitive state data that was analyzed using the set of layers and weights that were learned.

The network 2010, Internet, intranet, or another computer network, can be used for communication among various machines. An image and audio collection machine 2020 has a memory 2026 which stores instructions and one or more processors 2024 attached to the memory 2026, wherein the one or more processors 2024 can execute instructions. The image and audio collection machine 2020 can also have a network connection to carry cognitive state data 2060, and a display 2022 that can present cognitive state data, cognitive state profiles, mental state data, mental state profiles, emotional states, emotional state profiles, and so on. The image and audio collection machine 2020 can collect cognitive state data including image data, facial data, voice data, audio data, etc., from an occupant of a vehicle. In some embodiments, there are multiple image and audio collection machines 2020 that each collect cognitive state data including facial data. This type of collection machine can have a camera 2028 and/or a microphone 2030. In many embodiments, both a camera and a microphone will be present. Further embodiments include obtaining audio information and augmenting the analysis of the cognitive state data with the audio information. Once the cognitive state data 2060 has been collected, the image and audio collection machine 2020 can upload information to an analysis machine 2040, based on the cognitive state data from the occupant of the vehicle. The image and audio collection machine 2020 can communicate with the analysis machine 2040 over the network 2010, the Internet, some other computer network, or by another method suitable for communication between two machines. In some embodiments, the analysis machine 2040 functionality is embodied in the image and audio collection machine 2020.

The analysis machine 2040 can have a network connection for cognitive state information 2062, cognitive state profile information, or cognitive state data, a memory 2046 which stores instructions, and one or more processors 2044 attached to the memory 2046, wherein the one or more processors 2044 can execute instructions. The analysis machine 2040 can receive cognitive state information, collected from an occupant of the vehicle, from the image and audio collection machine 2020, and can learn a set of layers and weights based on the cognitive state data. The analysis machine 2040 can also compare further cognitive state data with the layers and weights while the occupant is in a second vehicle. In some embodiments, the analysis machine 2040 also allows a user to view and evaluate the cognitive state data, the layers and weights, cognitive state profiles for the occupant of the vehicle, and so on. The analysis machine 2040 can then provide the layer and weight information based on the cognitive information 2062 to the manipulation machine 2050. The cognitive state information and layers and weights can be presented on a display 2042. In some embodiments, the image and audio collection machine 2020 can also function as the manipulation machine 2050.

The manipulation machine 2050 can have a memory 2056 which stores instructions, and one or more processors 2054 attached to the memory 2056, wherein the one or more processors 2054 can execute instructions. The manipulation machine can use a computer network, the Internet, or another computer communication method, to request the cognitive state information 2062 from the analysis machine. The manipulation machine 2050 can receive vehicle manipulation information 2064, based on the cognitive state data 2060, from the occupant of the vehicle. The cognitive state information and vehicle manipulation information for the occupant can be presented on a display 2052. In some embodiments, the manipulation machine is set up to receive cognitive state data collected from an occupant of the vehicle, in a real-time or near real-time embodiment. In other embodiments, the manipulation machine is set up to receive the cognitive state data on an intermittent basis. In at least one embodiment, a single computer incorporates the image and audio collection machine, the analysis machine, and the manipulation machine functionalities.

In embodiments, a computer system for vehicle manipulation comprises: a memory which stores instructions; one or more processors attached to the memory wherein the one or more processors, when executing the instructions which are stored, are configured to: obtain one or more images of a first occupant of a first vehicle using a first imaging device within the first vehicle, wherein the one or more images include facial data of the first occupant; analyze, using a first computing device, the one or more images to determine cognitive state data for the first occupant; learn a set of layers and weights based on the cognitive state data; collect one or more images of a second occupant of a second vehicle, wherein the one or more images of the second occupant are analyzed to determine additional cognitive state data; and manipulate the second vehicle based on the additional cognitive state data that was analyzed using the set of layers and weights that were learned.

In embodiments, a computer program product embodied in a non-transitory computer readable medium for vehicle manipulation, the computer program product comprising code which causes one or more processors to perform operations of: obtaining one or more images of a first occupant of a first vehicle using a first imaging device within the first vehicle, wherein the one or more images include facial data of the first occupant; analyzing, using a first computing device, the one or more images to determine cognitive state data for the first occupant; learning a set of layers and weights based on the cognitive state data; collecting one or more images of a second occupant of a second vehicle, wherein the one or more images of the second occupant are analyzed to determine additional cognitive state data; and manipulating the second vehicle based on the additional cognitive state data that was analyzed using the set of layers and weights that were learned.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A computer-implemented method for vehicle manipulation comprising:
    obtaining one or more images of a first occupant of a first vehicle using a first imaging device within the first vehicle, wherein the one or more images include facial data of the first occupant;
    analyzing, using a first computing device, the one or more images to determine cognitive state data for the first occupant;
    learning a set of layers and weights based on the cognitive state data;
    collecting one or more images of a second occupant of a second vehicle, wherein the one or more images of the second occupant are analyzed to determine additional cognitive state data; and
    manipulating the second vehicle based on the additional cognitive state data that was analyzed using the set of layers and weights that were learned.

2. The method of claim 1 wherein the second vehicle is an autonomous or semiautonomous vehicle.

3. The method of claim 1 wherein the second occupant is a driver of the second vehicle.

4. The method of claim 1 wherein the second occupant is a passenger of the second vehicle.

5. The method of claim 1 wherein the manipulating includes warning the second occupant when the additional cognitive state data indicates inattentiveness.

6. The method of claim 1 wherein the manipulating includes passing control from the second occupant to the semiautonomous second vehicle based on the additional cognitive state data.

7. The method of claim 1 wherein the manipulating includes passing control from the second occupant to the autonomous second vehicle based on the additional cognitive state data.

8. The method of claim 1 wherein the first occupant and the second occupant are the same occupant.

9. The method of claim 1 further comprising augmenting the cognitive state data based on audio data collected on the first occupant.

10. The method of claim 1 further comprising augmenting the additional cognitive state data based on audio data collected on the second occupant.

11. The method of claim 10 wherein the audio data includes speech.

12. The method of claim 1 further comprising collecting, using a second imaging device, images of a person outside of the second vehicle, wherein the images of the person outside of the second vehicle are analyzed to determine cognitive state data for the person outside of the second vehicle.

13. The method of claim 12 wherein the person outside of the second vehicle is a pedestrian.

14. The method of claim 12 wherein the images of a person outside of the second vehicle include facial images of the person.

15. The method of claim 12 wherein the images of a person outside of the second vehicle include body posture images of the person.

16. The method of claim 12 further comprising further manipulating the second vehicle based on the cognitive state data for the person outside of the second vehicle.

17. The method of claim 16 wherein the further manipulating includes automatically slowing the second vehicle.

18. The method of claim 16 wherein the further manipulating includes notifying a custodial driver of the second vehicle.

19. The method of claim 1 further comprising augmenting the additional cognitive state data based on images from one or more additional vehicle occupants of the second vehicle.

20. The method of claim 1 further comprising tagging the cognitive state data with sensor data.

21. The method of claim 20 wherein the sensor data includes one or more of vehicle temperature, outside temperature, time of day, level of daylight, weather conditions, headlight activation, windshield wiper activation, entertainment center selection, or entertainment center volume.

22. The method of claim 1 wherein the learning is performed using a deep neural network.

23. The method of claim 22 wherein the learning is performed using a convolutional neural network.

24. A computer program product embodied in a non-transitory computer readable medium for vehicle manipulation, the computer program product comprising code which causes one or more processors to perform operations of:
    obtaining one or more images of a first occupant of a first vehicle using a first imaging device within the first vehicle, wherein the one or more images include facial data of the first occupant;
    analyzing, using a first computing device, the one or more images to determine cognitive state data for the first occupant;
    learning a set of layers and weights based on the cognitive state data;
    collecting one or more images of a second occupant of a second vehicle, wherein the one or more images of the second occupant are analyzed to determine additional cognitive state data; and
    manipulating the second vehicle based on the additional cognitive state data that was analyzed using the set of layers and weights that were learned.

25. A computer system for vehicle manipulation comprising:
    a memory which stores instructions;
    one or more processors attached to the memory wherein the one or more processors, when executing the instructions which are stored, are configured to:
        obtain one or more images of a first occupant of a first vehicle using a first imaging device within the first vehicle, wherein the one or more images include facial data of the first occupant;
        analyze, using a first computing device, the one or more images to determine cognitive state data for the first occupant;
        learn a set of layers and weights based on the cognitive state data;
        collect one or more images of a second occupant of a second vehicle,
    wherein the one or more images of the second occupant are analyzed to determine additional cognitive state data; and
        manipulate the second vehicle based on the additional cognitive state data that was analyzed using the set of layers and weights that were learned.

* * * * *